(12) United States Patent
King et al.

(10) Patent No.: US 9,951,126 B2
(45) Date of Patent: Apr. 24, 2018

(54) ANTIBODIES DIRECTED AGAINST NERVE GROWTH FACTOR (NGF)

(71) Applicant: AnaptysBio, Inc., San Diego, CA (US)

(72) Inventors: David J. King, Encinitas, CA (US); Peter Bowers, San Diego, CA (US); Robert A. Horlick, San Diego, CA (US); Tamlyn Yee Neben, Del Mar, CA (US)

(73) Assignee: AnaptysBio, Inc., San Diego, CA (US)

( * ) Notice: Subject to any disclaimer, the term of this patent is extended or adjusted under 35 U.S.C. 154(b) by 0 days.

(21) Appl. No.: 14/587,479

(22) Filed: Dec. 31, 2014

(65) Prior Publication Data

US 2015/0118226 A1    Apr. 30, 2015

Related U.S. Application Data

(63) Continuation of application No. 13/659,308, filed on Oct. 24, 2012, now Pat. No. 8,926,978.

(60) Provisional application No. 61/551,011, filed on Oct. 25, 2011.

(51) Int. Cl.
    *C07K 16/22* (2006.01)
    *C07H 21/04* (2006.01)

(52) U.S. Cl.
    CPC ............ *C07K 16/22* (2013.01); *C07H 21/04* (2013.01); *C07K 2317/21* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS

| | | | |
|---|---|---|---|
| 5,844,092 A | 12/1998 | Presta et al. | |
| 5,877,016 A | 3/1999 | Presta et al. | |
| 6,153,189 A | 11/2000 | Presta et al. | |
| 7,601,818 B2 | 10/2009 | Wild, Jr. et al. | |
| 2009/0123464 A1 | 5/2009 | Pavone et al. | |

FOREIGN PATENT DOCUMENTS

| | | |
|---|---|---|
| WO | WO 2001/064247 A2 | 9/2001 |
| WO | WO 2001/078698 A2 | 10/2001 |
| WO | WO 2002/096458 A1 | 12/2002 |
| WO | WO 2004/032870 A2 | 4/2004 |
| WO | WO 2005/044293 A2 | 5/2005 |
| WO | WO 2005/061540 A2 | 7/2005 |
| WO | WO 2006/131951 A2 | 12/2006 |

OTHER PUBLICATIONS

Geysen et al, J Molecular Recognition 1 (1988): 32-41.*
Foote et al, J. Mol. Biol. 224 (1992): 487-499.*
Aloe et al., *Arthritis and Rheumatism*, 35: 351-355 (1992).
Aloe et al., *Growth Factors*, 9: 149-155 (1993).
Apfel et al., *Neurology*, 51: 695-702 (1998).
Calissano et al., *Dev. Neurobiol.*, 70(5): 372-383 (2010).
Cattaneo, *Curr. Opin. Mol. Ther.*, 12(1): 94-106 (2010).
Chuang et al., *Nature*, 411: 957-962 (2001).
Djouhri et al., *J. Neurosci.*, 21: 8722-8733 (2001).
Freeman et al., *Prog. Brain Res.*, 146: 111-126 (2004).
Freund et al., *Prog. Brain Res.*, 146: 335-346 (2004).
Glanville et al., *Proc. Natl. Acad. Sci. USA*, 106: 20216-20221 (2009).
Harpf et al., *Muscle Nerve*, 25: 612-615 (2002).
Hefti et al., *Trends in Pharmacological Sciences*, 27: 85-91 (2006).
Hongo et al., *Hybridoma*, 19: 215-227 (2000).
Horigome et al., *J. Biol. Chem.*, 268: 14881-14887 (1993).
Horlick et al., *Gene*, 243: 187-194 (2000).
Julius et al., *Nature*, 413: 203-210 (2001).
Kawamoto et al., *J. Immunol.*, 168: 6412-6419 (2002).
Knappik et al., *J. Mol. Biol.*, 296: 57-86 (2000).
Krause et al., *MBio*, 2: e00345-10 (2011).
Lee et al., *Science*, 294: 1945-1948 (2001).
Levi-Montalcini, *Trends in Neurosciences*, 19(11): 514-520 (1996).
Lewin et al., *Eur. J. Neurosci.*, 6: 1903-1912 (1994).
Miura et al., *Mol. Med.*, 9: 166-174 (2003).
Patel et al., *Neuron*, 25(2): 345-357 (2000).
Ramer et al., *Eur. J. Neurosci.*, 11: 837-846 (1999).
Ro et al., *Pain*, 79: 265-274 (1999).
Ruberti et al., *Cell. Mol. Biol.*, 13: 559-568 (1993).
Shu et al., *Neurosci. Lett.*, 274: 159-162 (1999).
Sofroniew et al., *Annu. Rev. Neurosci.*, 24: 1217-1281 (2001).
Watson et al., *Bio Drugs*, 22(6): 349-359 (2008).
Weinstein et al., *Science*, 324: 807-810 (2009).
Woolf et al., *J. Neurosci.*, 16: 2716-2723 (1996).
Wu et al., *Science*, 333: 1593-1602 (2011).
Zhu et al., *J. Clin. Oncol.* 17: 2419-2428 (1999).

* cited by examiner

*Primary Examiner* — Robert C Hayes
(74) *Attorney, Agent, or Firm* — Leydig, Voit & Mayer, Ltd.

(57) ABSTRACT

The invention relates to an isolated immunoglobulin heavy chain polypeptide and an isolated immunoglobulin light chain polypeptide that binds to Nerve Growth Factor (NGF). The invention provides an NGF-binding agent that comprises the aforementioned immunoglobulin heavy chain polypeptide and immunoglobulin light chain polypeptide. The invention also provides vectors, compositions, and methods of using the NGF-binding agent to treat an NGF-mediated disease.

2 Claims, No Drawings

ANTIBODIES DIRECTED AGAINST NERVE GROWTH FACTOR (NGF)

CROSS-REFERENCE TO RELATED APPLICATIONS

This patent application is a continuation of copending U.S. patent application Ser. No. 13/659,308, filed Oct. 24, 2012, which claims the benefit of U.S. Provisional Patent Application No. 61/551,011, filed Oct. 25, 2011, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,514 Byte ASCII (Text) file named "719483 ST25.TXT," created on Dec. 31, 2014.

BACKGROUND OF THE INVENTION

Nerve growth factor (NGF) is a small secreted protein that is involved in the regulation of growth and differentiation of sympathetic and sensory neurons (Levi-Montalcini, *Science*, 294: 1945-1948 (2001), and Freeman et al., *Prog. Brain Res.*, 146: 111-126 (2004)). NGF is involved in a variety of processes involving signaling, such as cell differentiation and survival, growth cessation, and apoptosis of neurons. These events are mediated by NGF as a result of binding to its two cell-surface receptors, TrkA and p75. TrkA is a receptor with tyrosine kinase activity that forms a high-affinity binding site for NGF.

The role of NGF in neural development has been characterized extensively (see, e.g., Patel et al., *Neuron*, 25(2): 345-357 (2000)), but recent findings suggest that NGF plays a role in a variety of biological pathways, and that developmental effects are only one aspect of the biology of NGF. For example, endogenous NGF signaling is involved in neuroprotective and repair functions (see, e.g., Sofroniew et al., *Annu. Rev. Neurosci.*, 24: 1217-1281 (2001)). NGF signaling also has been implicated in Alzheimer's disease (see, e.g., Calissano et al., *Dev. Neurobiol.*, 70(5): 372-383 (2010)), inflammation (see, e.g., Freund et al., *Prog. Brain Res.*, 146: 335-346 (2004), and Levi-Montalcini, *Trends in Neurosciences*, 19(11): 514-520 (1996)), and pain transduction mechanisms (see, e.g., Watson et al., *Bio Drugs*, 22(6): 349-359 (2008), and Cattaneo, *Curr. Opin. Mol. Ther.*, 12(1): 94-106 (2010)).

The expression of NGF is high in injured and inflamed tissues, and activation of TrkA on nociceptive neurons triggers and potentiates pain signaling by multiple mechanisms (see, e.g., Hefti et al., *Trends in Pharmacological Sciences*, 27: 85-91 (2006)). Both local and systemic administration of NGF have been shown to elicit hyperalgesia and allodynia (Lewin et al., *Eur. J. Neurosci.*, 6: 1903-1912 (1994)). Intravenous infusion of NGF in humans produces a whole body myalgia while local administration evokes injection site hyperalgesia and allodynia in addition to the systemic effects (Apfel et al., *Neurology*, 51: 695-702 (1998)). Endogenous NGF also has been implicated in conditions in which pain is a prominent feature. For example, NGF is upregulated in dorsal root ganglion (DRG) Schwann cells for at least two months following peripheral nerve injury, and increased levels of NGF have been reported in the joints of animal models of arthritis (see, e.g., Aloe et al., *Growth Factors*, 9: 149-15 (1993)). In humans, NGF levels are elevated in synovial fluid from patients with rheumatoid or other types of arthritis (see, e.g., Aloe et al., *Arthritis and Rheumatism*, 35: 351-355 (1992)).

Inhibition of NGF function has been shown to prevent hyperalgesia and allodynia in models of neuropathic and chronic inflammatory pain. For example, in animal models of neuropathic pain, systemic injection of neutralizing antibodies to NGF inhibits both allodynia and hyperalgesia (see, e.g., Ramer et al., *Eur. J. Neurosci.*, 11: 837-846 (1999), and Ro et al., *Pain*, 79: 265-274 (1999)). Other antibodies specific for NGF have been described (see, e.g., U.S. Pat. Nos. 5,844,092, 5,877,016, 6,153,189, and 7,601,818; U.S. Patent Application Publication No. 2009/0123464 A1, International Patent Application Publication Nos. WO 2001/78698, WO 2001/64247, WO 2002/096458, WO 2004/032870, WO 2005/044293, WO 2005/061540, and WO 2006/131951; Hongo et al., *Hybridoma*, 19: 215-227 (2000), and Hongo et al., *Cell. Mol. Biol.*, 13: 559-568 (1993)). However, the therapeutic utility of currently available NGF antibodies is limited by their sub-optimum pharmacokinetics, stability, and efficacy in vivo.

Therefore, there is a need for an NGF-binding agent (e.g., an antibody) which binds NGF with a high affinity, exhibits increased stability and improved pharmacokinetics, and effectively neutralizes NGF activity in vivo. The invention provides such NGF binding agents.

BRIEF SUMMARY OF THE INVENTION

The invention provides an isolated immunoglobulin heavy chain polypeptide comprising one or both of the following: (a) a complementarity determining region-1 (CDR1) comprising SEQ ID NO: 1, wherein one or more of residues 3, 6, and 8 of SEQ ID NO: 1 are replaced with a different amino acid residue, and optionally one or more of residues 2, 4, 5, 7, and 9 are replaced with a different residue, and (b) a complementarity determining region-2 (CDR2) comprising SEQ ID NO: 2, except that one or more of residues 1, 4, 7, and 8 of SEQ ID NO: 2 are replaced with a different amino acid residue, and optionally one or more of residues 2, 3, 5, 6, 9, 10, 11, 12, 13, 14, 15, and 16 are replaced with a different residue.

The invention provides an isolated immunoglobulin heavy chain polypeptide which comprises an amino acid sequence selected from the group consisting of (a) an amino acid sequence that is at least 90% identical to SEQ ID NO: 3, (b) an amino acid sequence that is at least 90% identical to SEQ ID NO: 4, (c) an amino acid sequence that is at least 90% identical to SEQ ID NO: 5, and (d) an amino acid sequence that is at least 90% identical to SEQ ID NO: 6.

The invention provides an isolated immunoglobulin heavy chain polypeptide which comprises CDR1, CDR2, or both CDR1 and CDR2 of an amino acid sequence selected from the group consisting of SEQ ID NO: 3, SEQ ID NO: 4, SEQ ID NO: 5, and SEQ ID NO: 6.

The invention provides an isolated immunoglobulin light chain polypeptide comprising an amino acid sequence that is at least 80% identical to SEQ ID NO: 7, wherein at least one or more of residues 43, 71, and 87 of SEQ ID NO: 7 are replaced with a different residue.

The invention provides an isolated immunoglobulin light chain polypeptide comprising an amino acid sequence that is at least 80% identical to SEQ ID NO: 8, wherein at least one or more of residues 43, 71, and 87 of SEQ ID NO: 8 are replaced with a different residue.

The invention provides an isolated immunoglobulin light chain polypeptide which comprises an amino acid sequence selected from the group consisting of (a) an amino acid sequence that is at least 90% identical to SEQ ID NO: 9, (b) an amino acid sequence that is at least 90% identical to SEQ ID NO: 10, (c) an amino acid sequence that is at least 90% identical to SEQ ID NO: 11, (d) an amino acid sequence that is at least 90% identical to SEQ ID NO: 12, and (e) an amino acid sequence that is at least 90% identical to SEQ ID NO: 13

The invention provides an isolated immunoglobulin heavy chain polypeptide. The immunoglobulin heavy chain polypeptide comprises one or more amino acid sequences selected from the group consisting of (a) the amino acid sequence of SEQ ID NO: 14, (b) an amino acid sequence that is at least 95% identical to SEQ ID NO: 14, (c) an amino acid sequence that is at least 95% identical to SEQ ID NO: 14, wherein at least residue 31 of SEQ ID NO: 14 is replaced with a different amino acid residue, and optionally one or more of residues 24, 30, 44, 45, and 56 of SEQ ID NO: 14 is replaced with a different residue, and (d) an amino acid sequence that is at least 85% identical to SEQ ID NO: 14, wherein (i) residue 31 of SEQ ID NO: 14 is replaced with a different amino acid residue, and (ii) an alanine (A) residue, a glycine (G) residue, an amino acid sequence comprising FSNYAIS (SEQ ID NO: 32) and/or an amino acid sequence comprising FSNYAIN (SEQ ID NO: 33) is inserted into SEQ ID NO: 14.

The invention provides an isolated immunoglobulin heavy chain polypeptide which comprises an amino acid sequence selected from the group consisting of (a) an amino acid sequence that is at least 90% identical to SEQ ID NO: 15, (b) an amino acid sequence that is at least 90% identical to SEQ ID NO: 16, (c) an amino acid sequence that is at least 90% identical to SEQ ID NO: 17, (d) an amino acid sequence that is at least 90% identical to SEQ ID NO: 18, (e) an amino acid sequence that is at least 90% identical to SEQ ID NO: 19, (f) an amino acid sequence that is at least 90% identical to SEQ ID NO: 20, (g) an amino acid sequence that is at least 90% identical to SEQ ID NO: 21, (h) an amino acid sequence that is at least 90% identical to SEQ ID NO: 22, (i) an amino acid sequence that is at least 90% identical to SEQ ID NO: 23, (j) an amino acid sequence that is at least 90% identical to SEQ ID NO: 24, (k) an amino acid sequence that is at least 90% identical to SEQ ID NO: 25, (l) an amino acid sequence that is at least 90% identical to SEQ ID NO: 26, (m) an amino acid sequence that is at least 90% identical to SEQ ID NO: 27, (n) an amino acid sequence that is at least 90% identical to SEQ ID NO: 28, and (o) an amino acid sequence that is at least 90% identical to SEQ ID NO: 29.

The invention provides an isolated immunoglobulin heavy chain polypeptide which comprises one or more CDRs of an immunoglobulin heavy chain polypeptide comprising an amino acid sequence selected from the group consisting of SEQ ID NOs: 14-29.

The invention provides an isolated immunoglobulin light chain polypeptide comprising an amino acid sequence that is at least 97% identical to SEQ ID NO: 30.

The invention provides an isolated immunoglobulin light chain polypeptide which comprises an amino acid sequence that is at least 97% identical to SEQ ID NO: 31.

The invention provides a method of treating an NGF-mediated disorder in a mammal, especially a human, which comprises administering to the mammal a composition comprising an NGF-binding agent that comprises an aforementioned immunoglobulin heavy chain polypeptide and/or an aforementioned immunoglobulin light chain polypeptide, whereupon the NGF-mediated disorder is treated in the mammal.

DETAILED DESCRIPTION OF THE INVENTION

The invention provides an immunoglobulin heavy chain polypeptide and/or an isolated immunoglobulin light chain polypeptide, or a fragment (e.g., immunogenic fragment) thereof. The term "immunoglobulin" or "antibody," as used herein, refers to a protein that is found in blood or other bodily fluids of vertebrates, which is used by the immune system to identify and neutralize foreign objects, such as bacteria and viruses. A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($CH_1$, $CH_2$ and $CH_3$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding. The four framework regions (FWs or FRs) largely adopt a beta-sheet conformation, and the CDRs form loops connecting, and in some cases comprising part of, the beta-sheet structure. The constant regions of the light and heavy chains are not directly involved in binding of the antibody to an antigen, but exhibit various effector functions, such as participation in antibody-dependent cellular toxicity via interactions with effector molecules and cells.

The isolated immunoglobulin heavy chain polypeptide and the immunoglobulin light chain polypeptide of the invention desirably bind to nerve growth factor (NGF). As discussed above, NGF is involved in a variety of biological processes, including mediation of pain. In this respect, the development of sensitive nociceptive neurons depends in large part on NGF (see, e.g., Julius and Basbaum, *Nature*, 413: 203-210 (2001), and Shu and Mendell, *Neurosci. Lett.*, 274: 159-162 (1999)). Nociceptive neurons, following chronic inflammation, develop alterations in the frequency and duration of their action potential. These phenomena are inhibited by blocking endogenous NGF, leading to a significant attenuation of the hyperexcitability typical of states of chronic pain (see, e.g., Djouhri et al., *J. Neurosci.*, 21: 8722-8733 (2001)). NGF action in defining the pain threshold in adult nociceptors is mediated by the TrkA receptor, and also through modulation of the response mediated by the VR1 receptor present on the nociceptive terminals. The TrkA-dependent potentiation of the VR1 response is thought to occur through the intracellular transduction pathway of the phospholipase C gamma (PLC gamma) (Chuang et al., *Nature*, 411: 957-962 (2001)). NGF is released by mast cells, fibroblasts, and other cell types in the peripheral sites where inflammatory processes occur (Woolf et al., *J. Neurosci.*, 16: 2716-2723 (1996)). As these cells produce NGF, they are able to respond to NGF itself in the presence of lysophosphatidylserine (see, e.g., Horigome et al., *J. Biol. Chem.*, 268: 14881-14887 (1993), and Kawamoto et al., *J. Immunol.*, 168: 6412-6419 (2002)). As such, the NGF/TrkA system appears to mediate mastocyte activation through an autocrine positive feedback mechanism which allows local amplification of the algogenic inflammatory signal. High levels of NGF are also found in neurons, where NGF is apparently responsible for the modifications of nerve fibers associated with pain (see, e.g., Harpf et al., *Muscle Nerve*, 25: 612-615 (2002)). In certain forms of cancer, excess NGF facilitates the growth and infiltration of nerve fibers with induction of oncological pain (see, e.g., Zhu et al., *J. Clin. Oncol.* 17: 2419-2428 (1999)).

The amino acid sequence of several immunoglobulin heavy chain and light chain polypeptides which bind the NGF protein are known in the art (see, e.g., International Patent Application Publication Nos. WO 2005/044293, WO 2005/061540, and WO 2006/131951, and U.S. Patent Application Publication No. 20090123464 A1).

One example of an immunoglobulin heavy chain polypeptide that binds to NGF comprises a CDR1 comprising the amino acid sequence of SEQ ID NO: 1 and a CDR2 comprising the amino acid sequence of SEQ ID NO: 2. In one embodiment of the invention, the immunoglobulin heavy chain polypeptide comprises one or both of (a) a CDR1 comprising SEQ ID NO: 1, wherein one or more of residues 3, 6, and 8 of SEQ ID NO: 1 are replaced with a different amino acid residue, and optionally one or more of residues 2, 4, 5, 7, and 9 are replaced with a different residue, and (b) a CDR2 comprising SEQ ID NO: 2, except that one or more of residues 1, 4, 7, and 8 of SEQ ID NO: 2 are replaced with a different amino acid residue, and optionally one or more of residues 2, 3, 5, 6, 9, 10, 11, 12, 13, 14, 15, and 16 are replaced with a different residue. Each of amino acid residues 3, 6, and 8 of SEQ ID NO: 1, and/or each of amino acid residues 1, 4, 7, and 8 of SEQ ID NO: 2 can be replaced with any suitable amino acid residue that can be the same or different in each position. An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz, G. E. and R. H. Schirmer, supra).

Examples of conservative amino acid substitutions include substitutions of amino acids within the sub-groups described above, for example, lysine for arginine and vice versa such that a positive charge may be maintained; glutamic acid for aspartic acid and vice versa such that a negative charge may be maintained; serine for threonine such that a free —OH can be maintained; and glutamine for asparagine such that a free —NH$_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In one embodiment, the isolated immunoglobulin heavy chain polypeptide comprises either (a) a CDR1 comprising SEQ ID NO: 1, wherein one or more of residues 3, 6, and 8 of SEQ ID NO: 1 are replaced with a different amino acid residue, and optionally one or more of residues 2, 4, 5, 7, and 9 are replaced with a different residue, or (b) a CDR2 comprising SEQ ID NO: 2, except that one or more of residues 1, 4, 7, and 8 of SEQ ID NO: 2 are replaced with a different amino acid residue, and optionally one or more of residues 2, 3, 5, 6, 9, 10, 11, 12, 13, 14, 15, and 16 are replaced with a different residue. In another embodiment, the isolated immunoglobulin heavy chain polypeptide comprises both (a) a CDR1 comprising SEQ ID NO: 1, wherein one or more of residues 3, 6, and 8 of SEQ ID NO: 1 are replaced with a different amino acid residue, and optionally one or more of residues 2, 4, 5, 7, and 9 are replaced with a different residue, and (b) a CDR2 comprising SEQ ID NO: 2, except that one or more of residues 1, 4, 7, and 8 of SEQ ID NO: 2 are replaced with a different amino acid residue, and optionally one or more of residues 2, 3, 5, 6, 9, 10, 11, 12, 13, 14, 15, and 16 are replaced with a different residue.

In a preferred embodiment, the isolated immunoglobulin heavy chain polypeptide comprises a CDR1 comprising SEQ ID NO: 1, wherein (a) residue 3 of SEQ ID NO: 1 is replaced with an F (phenylalanine) residue, (b) residue 6 of SEQ ID NO: 1 is replaced with a Y (tyrosine) residue, (c) residue 8 of SEQ ID NO: 1 is replaced with an M (methionine) residue, or any combination of the foregoing replacements.

In another preferred embodiment, the isolated immunoglobulin heavy chain polypeptide comprises a CDR1 comprising SEQ ID NO: 2, wherein (a) residue 1 of SEQ ID NO: 2 is replaced with a V (valine) residue, (b) residue 4 of SEQ ID NO: 2 is replaced with a T (threonine) residue, (c) residue 7 of SEQ ID NO: 2 is replaced with a T (threonine) reside or an S (serine) residue, (d) residue 8 of SEQ ID NO: 2 is replaced with an R (arginine) residue or an N (asparagine) residue, or any combination of the foregoing replacements.

In addition to the amino acid substitutions discussed above, the immunoglobulin heavy chain polypeptide optionally can comprise additional amino acid substitutions. In one embodiment, the immunoglobulin heavy chain polypeptide comprises a CDR1 comprising SEQ ID NO: 1, wherein additionally one or more of residues 2, 4, 5, 7, and 9 are replaced with a different residue. Each of the amino acids at residues 2, 4, 5, 7, and 9 of SEQ ID NO: 1 can be replaced with any suitable amino acid residue that can be the same or different in each position. For example, the immunoglobulin heavy chain polypeptide can comprise a CDR1 comprising SEQ ID NO: 1, wherein one or more of residues 3, 6, and 8 of SEQ ID NO: 1 are replaced with a different amino acid residue, and residue 2 of SEQ ID NO: 1 is replaced with a T (threonine) residue, residue 4 of SEQ ID NO: 1 is replaced with an N (asparagine) residue, residue 5 of SEQ ID NO: 1 is replaced with a T (threonine) residue, residue 7 of SEQ ID NO: 1 is replaced with an S (serine) residue, residue 9 of SEQ ID NO: 1 is replaced with an N (asparagine) residue, or any combination of the foregoing replacements. In another embodiment, the immunoglobulin can comprise a CDR2 comprising SEQ ID NO: 2, wherein additionally one or more of residues 2, 3, 5, 6, 9, 10, 11, 12, 13, 14, 15, and 16 are replaced with a different residue. Each of the amino acids at residues 2, 3, 5, 6, 9, 10, 11, 12, 13, 14, 15, and 16 of SEQ ID NO: 2 can be replaced with any suitable amino acid residue that can be the same or different in each position. For example, the immunoglobulin heavy chain polypeptide can comprise a CDR2 comprising SEQ ID NO: 2, wherein one or more of residues 1, 4, 7, and 8 of SEQ ID NO: 2 are replaced with a different amino acid residue, and (a) residue 2 of SEQ ID NO: 2 is replaced with an I (isoleucine) residue, (b) residue 9 of SEQ ID NO: 2 is replaced with a S (serine) residue, (c) residue 5 of SEQ ID NO: 2 is replaced with a T (threonine) residue, (d) residue 11 of SEQ ID NO: 2 is replaced with a Y (tyrosine) residue, (e) residue 12 of SEQ ID NO: 2 is replaced with a D (aspartic acid) residue or a Y (tyrosine) residue, (f) residue 13 of SEQ ID NO: 2 is replaced with an S (serine) residue, (g) residue 14 of SEQ ID NO: 2 is replaced with a V (valine residue), (h) residue 16 of SEQ ID NO: 2 is replaced with a G (glycine) residue, or any combination of the foregoing replacements.

The invention provides an isolated immunoglobulin heavy chain polypeptide which comprises an amino acid sequence selected from the group consisting of (a) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 3, (b) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 4, (c) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 5, and (d) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 6.

Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.,* 215(3): 403-410 (1990), Beigert et al., *Proc. Natl. Acad. Sci. USA,* 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)).

Exemplary immunoglobulin heavy chain polypeptides as described above can comprise any one of the following amino acid sequences: SEQ ID NO: 3, SEQ ID NO: 4, SEQ ID NO: 5, and SEQ ID NO: 6.

The invention also provides an isolated immunoglobulin heavy chain polypeptide which comprises CDR1, CDR2, or both CDR1 and CDR2 of an amino acid sequence selected from the group consisting of SEQ ID NO: 3, SEQ ID NO: 4, SEQ ID NO: 5, and SEQ ID NO: 6. In one embodiment, the isolated immunoglobulin heavy chain polypeptide comprises only one of CDR1 and CDR2 of an amino acid sequence selected from the group consisting of SEQ ID NO: 3, SEQ ID NO: 4, SEQ ID NO: 5, and SEQ ID NO: 6. In another embodiment, the isolated immunoglobulin heavy chain polypeptide comprises both CDR1 and CDR2 of an amino acid sequence selected from the group consisting of SEQ ID NO: 3, SEQ ID NO: 4, SEQ ID NO: 5, and SEQ ID NO: 6. Alternatively, the isolated immunoglobulin heavy chain polypeptide can comprise CDR1, CDR2, and CDR3 of an amino acid sequence selected from the group consisting of SEQ ID NO: 3, SEQ ID NO: 4, SEQ ID NO: 5, and SEQ ID NO: 6. The locations of the CDRs of each of SEQ ID NOs: 3-6 are set forth in Table 1.

TABLE 1

| SEQ ID NO | Location of CDR1 (residues of SEQ ID NO) | Location of CDR2 (residues of SEQ ID NO) | Location of CDR3 (residues of SEQ ID NO) |
|---|---|---|---|
| 3 | 27-35 (inclusive) | 50-66 (inclusive) | 99-112 (inclusive) |
| 4 | 27-35 (inclusive) | 50-66 (inclusive) | 99-112 (inclusive) |
| 5 | 27-35 (inclusive) | 50-66 (inclusive) | 99-112 (inclusive) |
| 6 | 27-35 (inclusive) | 50-66 (inclusive) | 99-112 (inclusive) |

The invention provides an isolated immunoglobulin light chain polypeptide comprising an amino acid sequence that is at least 80% identical (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical) to SEQ ID NO: 7, or an amino acid sequence that is at least 80% identical (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical) to SEQ ID NO: 8, wherein at least one or more of residues 43, 71, and 87 of SEQ ID NO: 7 or SEQ ID NO: 8 are replaced with a different residue. Each of the amino acids at residues 43, 71, and 87 of SEQ ID NO: 7 or SEQ ID NO: 8 can be replaced with any suitable amino acid residue that can be the same or different in each position. In one embodiment, only one of residues 43, 71, or 87 of SEQ ID NO: 7 or SEQ ID NO: 8 is replaced with a different amino acid residue. In another embodiment, each of two of residues 43, 71, or 87 of SEQ ID NO: 7 or SEQ ID NO: 8 is replaced with a different amino acid residue. Preferably, each of residues 43, 71, and 87 of SEQ ID NO: 7 or SEQ ID NO: 8 is independently replaced with a different amino acid residue. For example, (a) residue 43 of SEQ ID NO: 7 or SEQ ID NO: 8 is replaced with a V (valine) residue, (b) residue 71 of SEQ ID NO: 7 or SEQ ID NO: 8 is replaced with an F (phenylalanine) residue or a L (lysine) residue, (c) residue 87 of SEQ ID NO: 7 or SEQ ID NO: 8 is replaced with a Y (tyrosine) residue, or any combination of the foregoing replacements. An exemplary immunoglobulin light chain polypeptide can comprise the amino acid sequence of SEQ ID NO: 9.

In addition to the amino acid substitutions discussed above, the aforementioned immunoglobulin light chain polypeptide optionally can comprise additional amino acid substitutions. In one embodiment, the immunoglobulin light chain polypeptide further comprises an amino acid substitution at at least one residue selected from the group consisting of residues 66, 90, and 93 of SEQ ID NO: 7 or SEQ ID NO: 8. In this regard, the amino acid residue at positions 66, 90, and 93 of SEQ ID NO: 7 or SEQ ID NO: 8 can be replaced with any suitable amino acid residue as described herein. In one embodiment, residue 66 of SEQ ID NO: 7 or SEQ ID NO: 8 is replaced with an E (glutamic acid) residue, residue 90 of SEQ ID NO: 7 or SEQ ID NO: 8 is replaced with a Q (glutamine) residue, residue 93 of SEQ ID NO: 7 or SEQ ID NO: 8 is replaced with a D (aspartic acid) residue, or any combination of the foregoing replacements.

The invention also provides an isolated immunoglobulin light chain polypeptide which comprises an amino acid sequence selected from the group consisting of (a) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 9, (b) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 10, (c) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 11, (d) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 12, and (e) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 13.

Exemplary immunoglobulin light chain polypeptides as described above can comprise any one of the following amino acid sequences: SEQ ID NO: 9, SEQ ID NO: 10, SEQ ID NO: 11, SEQ ID NO: 12, and SEQ ID NO: 13.

The immunoglobulin heavy chain polypeptide can comprise an amino acid sequence that is at least 95% identical (e.g., at least 96%, at least 97%, at least 98%, or at least 99%) to SEQ ID NO: 14, such as an amino acid sequence that is 100% identical to SEQ ID NO: 14, i.e., the amino acid sequence of SEQ ID NO: 14. In another embodiment, the immunoglobulin heavy chain polypeptide can comprise an amino acid sequence that is at least 95% identical (e.g., at least 96%, at least 97%, at least 98%, at least 99%, or 100% identical) to SEQ ID NO: 14, wherein at least residue 31 of SEQ ID NO: 14 is replaced with a different amino acid residue, and optionally one or more of residues 24, 30, 44, 45, and 56 of SEQ ID NO: 14 is replaced with a different residue. The amino acid at residue 31 of SEQ ID NO: 14 can be replaced with any suitable amino acid residue. For example, the amino acid at residue 31 of SEQ ID NO: 14 can be replaced with an N (asparagine) residue. In addition to the amino acid substitution at residue 31 of SEQ ID NO: 14, one or more of residues 24, 30, 44, 45, and 56 of SEQ ID NO: 14 can be replaced with a different residue. Each of the amino acids at residues 24, 30, 44, 45, and 56 of SEQ ID NO: 14 can be replaced with any suitable amino acid residue that can be the same or different in each position. For example, the immunoglobulin heavy chain polypeptide can comprise an amino acid sequence that is at least 95% identical to SEQ ID NO: 14, wherein at least residue 31 of SEQ ID NO: 14 is replaced with a different amino acid residue, and (a) residue 24 of SEQ ID NO: 14 is replaced with a P (proline) residue, (b) residue 30 of SEQ ID NO: 14 is replaced with an N (asparagine) or an I (isoleucine) residue, (c) residue 44 of SEQ ID NO: 14 is replaced with an R (arginine) residue, (d) residue 45 of SEQ ID NO: 14 is replaced with an F (phenylalanine) residue, (e) residue 56 of SEQ ID NO: 14 is replaced with a D (aspartic acid) residue, or any combination of the foregoing replacements.

Exemplary immunoglobulin heavy chain polypeptides as described above can comprise any one of the following amino acid sequences: SEQ ID NO: 15, SEQ ID NO: 16, SEQ ID NO: 17, SEQ ID NO: 18, and SEQ ID NO: 19.

In another embodiment, the immunoglobulin heavy chain polypeptide comprises an amino acid sequence that is at least 85% identical to SEQ ID NO: 14, wherein (i) residue 31 of SEQ ID NO: 14 is replaced with a different amino acid residue, and (ii) an A (alanine) residue, a G (glycine) residue, an amino acid sequence comprising FSNYAIS (SEQ ID NO: 32), and/or an amino acid sequence comprising FSNYAIN (SEQ ID NO: 33) is inserted into SEQ ID NO: 14. The immunoglobulin heavy chain polypeptide comprises an amino acid sequence that is at least 85% identical (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical) to SEQ ID NO: 14, and the amino acid at residue 31 of SEQ ID NO: 14 can be replaced with any suitable amino acid residue. For example, the amino acid at residue 31 of SEQ ID NO: 14 can be replaced with an N (asparagine) residue. In addition, one or more amino acids can be inserted into the aforementioned immunoglobulin heavy chain polypeptide. Any number of any suitable amino acids can be inserted into the amino acid sequence of the immunoglobulin heavy chain polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin heavy chain polypeptide. Preferably, 1-10 amino acids (e.g., 2, 3, 4, 5, 6, 7, 8, or 9 amino acids) are inserted in to the amino acid sequence of the immunoglobulin heavy chain polypeptide. The amino acid(s) can be inserted into SEQ ID NO: 14 in any suitable location. Preferably, the amino acid(s) are inserted into a CDR (e.g., CDR1, CDR2, or CDR3) of SEQ ID NO: 14. For example, a G (glycine) residue or an A (alanine) residue can be inserted into SEQ ID NO: 14 after residue 34. Alternatively, an amino acid sequence comprising FSNYAIS (SEQ ID NO: 32) or FSNYAIN (SEQ ID NO: 33) can be inserted into SEQ ID NO: 14 at any location, and preferably into CDR1 of SEQ ID NO: 14.

Exemplary immunoglobulin heavy chain polypeptides as described above can comprise any one of the following amino acid sequences: SEQ ID NO: 17, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29.

The invention further provides an isolated immunoglobulin heavy chain polypeptide which comprises an amino acid sequence selected from the group consisting of (a) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 15, (b) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 16, (c) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 17, (d) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 18, (e) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 19, (f) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 20, (g) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 21, (h) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 22, (i) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 23, (j) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 24, (k) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 25, (l) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 26, (m) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 27, (n) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 28, and (o) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 29.

The invention also provides an isolated immunoglobulin heavy chain polypeptide which comprises one or more CDRs of an immunoglobulin heavy chain polypeptide comprising an amino acid sequence selected from the group consisting of SEQ ID NOs: 14-29. In one embodiment, the isolated immunoglobulin heavy chain polypeptide comprises only one CDR of an immunoglobulin heavy chain polypeptide comprising an amino acid sequence of any one of SEQ ID NOs: 14-29. In another embodiment, the isolated immunoglobulin heavy chain polypeptide can comprise a first CDR of an immunoglobulin heavy chain polypeptide comprising an amino acid sequence selected from the group consisting of SEQ ID NOs: 14-29, and (b) a second CDR of an immunoglobulin heavy chain polypeptide comprising an amino acid sequence selected from the group consisting of SEQ ID NOs: 14-29. Alternatively, the isolated immunoglobulin heavy chain polypeptide can comprise (a) a CDR1 of an immunoglobulin heavy chain polypeptide comprising an amino acid sequence selected from the group consisting of SEQ ID NOs: 14-29, (b) a CDR2 of an immunoglobulin heavy chain polypeptide comprising an amino acid sequence selected from the group consisting of SEQ ID NOs: 14-29, and (c) a CDR3 of an immunoglobulin heavy chain polypeptide comprising an amino acid sequence selected from the group consisting of SEQ ID NOs: 14-29. The locations of the CDRs of each of SEQ ID NOs: 14-19 are set forth in Table 2.

TABLE 2

| SEQ ID NO | Location of CDR1 (residues of SEQ ID NO) | Location of CDR2 (residues of SEQ ID NO) | Location of CDR3 (residues of SEQ ID NO) |
|---|---|---|---|
| 14 | 27-35 (inclusive) | 50-66 (inclusive) | 99-117 (inclusive) |
| 15 | 27-35 (inclusive) | 50-66 (inclusive) | 99-117 (inclusive) |
| 16 | 27-35 (inclusive) | 50-66 (inclusive) | 99-117 (inclusive) |
| 17 | 27-36 (inclusive) | 51-67 (inclusive) | 100-118 (inclusive) |
| 18 | 27-35 (inclusive) | 50-66 (inclusive) | 99-117 (inclusive) |
| 19 | 27-35 (inclusive) | 50-66 (inclusive) | 99-117 (inclusive) |
| 20 | 27-42 (inclusive) | 57-73 (inclusive) | 106-124 (inclusive) |
| 21 | 27-44 (inclusive) | 59-75 (inclusive) | 108-126 (inclusive) |
| 22 | 27-42 (inclusive) | 57-73 (inclusive) | 106-124 (inclusive) |
| 23 | 27-44 (inclusive) | 59-75 (inclusive) | 108-126 (inclusive) |
| 24 | 27-44 (inclusive) | 59-75 (inclusive) | 108-126 (inclusive) |
| 25 | 27-44 (inclusive) | 59-75 (inclusive) | 108-126 (inclusive) |
| 26 | 27-44 (inclusive) | 59-75 (inclusive) | 108-126 (inclusive) |
| 27 | 27-44 (inclusive) | 59-75 (inclusive) | 108-126 (inclusive) |
| 28 | 27-44 (inclusive) | 59-75 (inclusive) | 108-126 (inclusive) |
| 29 | 27-44 (inclusive) | 59-75 (inclusive) | 108-126 (inclusive) |

The invention provides an isolated immunoglobulin light chain polypeptide comprising an amino acid sequence that is at least 97% identical (e.g., at least 97.5%, at least 98%, at least 98.5%, at least 99%, at least 99.5%, or 100% identical) to SEQ ID NO: 30. In one embodiment, the isolated immunoglobulin light chain polypeptide comprises the amino acid sequence of SEQ ID NO: 30. In another embodiment, the isolated immunoglobulin light chain polypeptide comprises the amino acid sequence of SEQ ID NO: 30, wherein residue 40 of SEQ ID NO: 30 is replaced with a different amino acid residue. The amino acid at residue 40 of SEQ ID NO: 30 can be replaced with any suitable amino acid residue. For example, the amino acid at residue 40 of SEQ ID NO: 14 can be replaced with a T (tyrosine) residue. The invention also provides an isolated immunoglobulin light chain polypeptide which comprises an amino acid sequence that is at least 97% identical (e.g., at least 97.5%, at least 98%, at least 98.5%, at least 99%, at least 99.5%, or 100% identical) to SEQ ID NO: 31. Exemplary immunoglobulin light chain polypeptides as described above can comprise the amino acid sequence of SEQ ID NO: 30 or SEQ ID NO: 31.

In other embodiments, the invention provides one or more isolated nucleic acid sequences that encode one or more of any of the aforementioned immunoglobulin heavy chain polypeptides, e.g., the amino acid sequences of any of SEQ ID NOs: 3-6 and 14-29 or any of the variants and/or portions thereof as described herein. In addition, the invention provides one or more nucleic acid sequences that encode one or more of any of the aforementioned immunoglobulin light chain polypeptides, e.g., the amino acid sequences of any of SEQ ID NOs: 7-13, 30, and 31 or any of the variants and/or portions thereof as described herein. A "nucleic acid" is intended to encompass a polymer of DNA or RNA, i.e., a polynucleotide, which can be single-stranded or double-stranded and which can contain non-natural or altered nucleotides. Nucleic acids are typically linked via phosphate bonds to form nucleic acids or polynucleotides, though many other linkages are known in the art (e.g., phosphorothioates, boranophosphates, and the like).

The invention provides an isolated NGF-binding agent comprising the inventive immunoglobulin heavy chain polypeptide and/or the inventive immunoglobulin light chain polypeptide. By "NGF-binding agent" is meant a molecule, preferably a proteinaceous molecule, which specifically binds to NGF. Preferably, the NGF-binding agent is an antibody or a fragment (e.g., immunogenic fragment) thereof. The isolated NGF-binding agent of the invention comprises the inventive immunoglobulin heavy chain polypeptide, or a fragment thereof comprising at least five amino acids, and/or the inventive immunoglobulin light chain polypeptide, or a fragment thereof comprising at least five amino acids. In one embodiment, the isolated NGF-binding agent comprises the inventive immunoglobulin heavy chain polypeptide or the inventive immunoglobulin light chain polypeptide. In another embodiment, the isolated NGF-binding agent comprises both the inventive immunoglobulin heavy chain polypeptide and the inventive immunoglobulin light chain polypeptide.

The invention is not limited to an isolated NGF-binding agent comprising an immunoglobulin heavy chain polypeptide or light chain polypeptide having replacements of the specific amino acid residues disclosed herein. Indeed, any amino acid residue of the inventive immunoglobulin heavy chain polypeptide and/or the inventive immunoglobulin light chain polypeptide can be replaced, in any combination, with a different amino acid residue, so long as the biological activity of the NGF-binding agent is enhanced or improved as a result of the amino acid replacements. The "biological activity" of an NGF-binding agent refers to, for example, binding affinity for a particular NGF epitope, neutralization of NGF activity in vivo (e.g., $IC_{50}$), in vivo stability (including but not limited to thermal stability and proteolytic stability), pharmacokinetics, the immunogenic properties of the NGF-binding agent, and cross-reactivity (e.g., with non-human homologs or orthologs of NGF, or with other proteins or tissues). Other biological properties or characteristics of an antigen-binding agent recognized in the art include, for example, avidity, selectivity, solubility, folding, immunotoxicity, expression, formulation, and catalytic activity. The aforementioned properties or characteristics can be observed, measured, and/or assessed using standard techniques including, but not limited to, ELISA, competitive ELISA, BIACORE or KINEXA surface plasmon resonance analysis, in vitro or in vivo neutralization assays, receptor binding assays, cytokine or growth factor production and/or secretion assays, and signal transduction and immunohistochemistry assays.

The terms "inhibit" or "neutralize," as used herein with respect to the activity of an NGF-binding agent, refer to the ability to substantially antagonize, prohibit, prevent, restrain, slow, disrupt, eliminate, stop, or reverse the progression or severity of, for example, the biological activity of NGF, or a disease or condition associated with NGF. The isolated NGF-binding agent of the invention preferably inhibits or neutralizes the activity of an NGF by at least about 20%, about 30%, about 40%, about 50%, about 60%, about 70%, about 80%, about 90%, about 95%, about 100%, or a range defined by any two of the foregoing values.

The isolated NGF-binding agent of the invention can be a whole antibody, as described herein, or an antibody fragment. The terms "fragment of an antibody," "antibody fragment," or "functional fragment of an antibody" are used interchangeably herein to mean one or more fragments of an antibody that retain the ability to specifically bind to an antigen (see, generally, Holliger et al., *Nat. Biotech.*, 23(9): 1126-1129 (2005)). The isolated NGF-binding agent can contain any NGF-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $CH_1$ domains; (ii) a $F(ab')_2$ fragment, which is a bivalent fragment comprising two Fab fragments linked by a disulfide bridge at the hinge region; and (iii) a Fv fragment consisting of the $V_L$ and $V_H$ domains of a single arm of an antibody.

In embodiments where the isolated NGF-binding agent comprises a fragment of the inventive immunoglobulin heavy chain or light chain polypeptide, the fragment can be of any size so long as the fragment binds to, and preferably inhibits the activity of, NGF. In this respect, a fragment of the immunoglobulin heavy chain polypeptide desirably comprises between about 5 and 18 amino acids (e.g., about 5, 6, 7, 8, 9, 10, 11, 12, 13, 14, 15, 16, 17, 18, or a range defined by any two of the foregoing values). Similarly, a fragment of the immunoglobulin light chain polypeptide desirably comprises between about 5 and 18 amino acids (e.g., about 5, 6, 7, 8, 9, 10, 11, 12, 13, 14, 15, 16, 17, 18, or a range defined by any two of the foregoing values).

When the NGF-binding agent is an antibody or antibody fragment, the antibody or antibody fragment comprises a constant region ($F_c$) of any suitable class. Preferably, the antibody or antibody fragment comprises a constant region that is based upon wild type IgG1, IgG2, or IgG4 antibodies, or variants thereof.

The NGF-binding agent also can be a single chain antibody fragment. Examples of single chain antibody fragments include, but are not limited to, (i) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain (see, e.g., Bird et al., *Science*, 242: 423-426 (1988); Huston et al., *Proc. Natl. Acad. Sci. USA*, 85: 5879-5883 (1988); and Osbourn et al., *Nat. Biotechnol.*, 16: 778 (1998)) and (ii) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Patent Application Publication 2009/0093024 A1.

The isolated NGF-binding agent also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

The isolated NGF-binding agent can be, or can be obtained from, a human antibody, a non-human antibody, or a chimeric antibody. By "chimeric" is meant an antibody or fragment thereof comprising both human and non-human regions. Non-human antibodies include antibodies isolated from any non-human animal, such as, for example, a rodent (e.g., a mouse or rat). The immunoglobulin heavy chain polypeptide of the NGF-binding agent can be obtained from a human antibody, a non-human antibody, or a chimeric antibody, independent of whether the immunoglobulin light chain polypeptide of the NGF-binding agent is obtained from a human antibody, a non-human antibody, or a chimeric antibody. In other words, for example, the immunoglobulin heavy chain polypeptide can be obtained from a human antibody, and the immunoglobulin light chain polypeptide can be obtained from a non-human antibody. Conversely, the immunoglobulin heavy chain polypeptide can be obtained from a non-human antibody, and the immunoglobulin light chain polypeptide can be obtained from a human antibody. Alternatively, the immunoglobulin heavy chain polypeptide can be obtained from a rodent antibody, and the immunoglobulin light chain polypeptide can be obtained from a human antibody. This scenario may be useful, e.g., for the humanization of an antibody. In another embodiment, the immunoglobulin heavy chain polypeptide and the immunoglobulin light chain polypeptide are both obtained from a human antibody or a non-human antibody. Alternatively, the immunoglobulin heavy chain polypeptide and the immunoglobulin light chain polypeptide are both chimeric antibodies.

A human antibody, a non-human antibody, or a chimeric antibody can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and C. A. Janeway et al. (eds.), *Immunobiology, 5th Ed.*, Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.,* 23(9): 1117-25 (2005), and Lonberg, *Handb. Exp. Pharmacol.,* 181: 69-97 (2008)).

In another embodiment of the invention, the isolated NGF-binding agent can be part of an "alternative scaffold" or a fragment thereof. By "alternative scaffold" is meant a non-antibody polypeptide or polypeptide domain which displays an affinity and specificity towards an antigen of interest similar to that of an antibody. Exemplary alternative scaffolds include a β-sandwich domain such as from fibronectin (e.g., Adnectins), lipocalins (e.g., Anticalin), a Kunitz domain, thioredoxin (e.g., peptide aptamer), protein A (e.g., AFFIBODY™ molecules), an ankyrin repeat (e.g., DARPins), γ-β-crystallin or ubiquitin (e.g., AFFLIN™ molecules), CTLD3 (e.g., Tetranectin), and multivalent complexes (e.g., ATRIMER™ molecules or SIMP™ molecules). Alternative scaffolds are described in, for example, Binz et al., *Nat. Biotechnol.,* 23: 1257-1268 (2005); Skerra, *Curr. Opin. Biotech.,* 18: 295-304 (2007); and U.S. Patent Application Publication 2009/0181855 A1.

In one embodiment, the alternative scaffold can be an AVIMER™ molecule. An AVIMER™ molecule is a class of therapeutic proteins from human origin unrelated to antibodies and antibody fragments, which are composed of several modular and reusable binding domains, referred to as A-domains (also referred to as class A module, complement type repeat, or LDL-receptor class A domain). AVIMER™ molecules were developed from human extracellular receptor domains by in vitro exon shuffling and phage display (Silverman et al., *Nat. Biotechnol.,* 23: 1493-94 (2005), and Silverman et al., *Nat. Biotechnol.,* 24: 220 (2006)). AVIMER™ molecules may comprise multiple independent binding domains that may exhibit improved affinity (in some cases sub-nanomolar) and specificity compared with single-epitope binding proteins (see, e.g., U.S. Patent Application Publications 2005/0221384 A1; 2005/0164301 A1; 2005/0053973 A1; 2005/0089932 A1; 2005/0048512 A1; and 2004/0175756 A1). Each of the known 217 human A-domains comprises about 35 amino acids (about 4 kDa). Native A-domains fold quickly and efficiently to a uniform, stable structure mediated primarily by calcium binding and disulfide formation. A conserved scaffold motif of only twelve amino acids is required for this common structure. An AVIMER™ molecule comprises multiple A-domains which are separated from one another by linkers that average five amino acids in length. The end result is a single protein chain containing multiple domains, each of which represents a separate function. Each domain of an AVIMER™ molecule binds an antigen independently, and the energetic contributions of each domain are additive.

The invention also provides one or more isolated nucleic acid sequences that encode the aforementioned NGF-binding agent.

As discussed herein, portions of the inventive isolated immunoglobulin heavy chain polypeptide (e.g., CDRs) can be inserted into other molecules (e.g., polypeptides) to generate novel molecules which bind an antigen of interest. Similarly, portions of the inventive isolated immunoglobulin light chain polypeptide can be inserted into other molecules (e.g., polypeptides) to generate novel molecules which bind an antigen of interest. Such novel antigen-binding molecules can be generated using routine molecular biology techniques known in the art. In one embodiment, a CDR (e.g., CDR1, CDR2, or CDR3) or a variable region of the immunoglobulin heavy chain polypeptide and/or the immunoglobulin light chain polypeptide described herein can be transplanted (i.e., grafted) into another molecule, such as an antibody or non-antibody polypeptide, using either protein chemistry or recombinant DNA technology. In this regard, the invention also provides an isolated NGF-binding agent comprising at least one CDR of an immunoglobulin heavy chain and/or light chain polypeptide as described herein.

In another embodiment, the entire variable region of the immunoglobulin heavy chain polypeptide and/or the immunoglobulin light chain polypeptide described herein can be transplanted in place of the variable region of a LC and/or a HC of another antibody.

The aforementioned methods and molecules may be useful, for example, to generate an antibody comprising an Fc region of a different isotype or an Fc region that is conjugated to a protein or non-protein moiety (e.g., a fluorescent tag or a chemotherapeutic agent). The invention also provides a conjugate of (1) an antibody, an alternative scaffold, or fragments thereof, and (2) a protein or non-protein moiety comprising the NGF-binding agent. For example, the NGF-binding agent can be part of an antibody conjugated to a peptide, a fluorescent molecule, or a chemotherapeutic agent.

The invention further provides a vector comprising a nucleic acid sequence encoding the inventive immunoglobulin heavy chain polypeptide, a nucleic acid sequence encoding the inventive immunoglobulin light chain polypeptide, or one or more nucleic acid sequences encoding the isolated NGF-binding agent. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual, 3rd edition,* Cold Spring Harbor Press, Cold Spring Harbor, N.Y. (2001), and Ausubel et al., *Current Protocols in Molecular Biology,* Greene Publishing Associates and John Wiley & Sons, New York, N.Y. (1994)).

In addition to the nucleic acid sequence encoding the immunoglobulin heavy chain polypeptide, the immunoglobulin light chain polypeptide, or the NGF-binding agent, the vector preferably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology,* Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.,* 93: 3346-3351 (1996)), the T-REX™ system (Invitrogen, Carlsbad, Calif.), LACSWITCH™ System (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), *Fundamental Immunology*, 3rd Edition, Raven Press, New York (1993), pages 353-363; and U.S. Pat. No. 5,885,827).

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA*, 77: 3567-3570 (1980); O'Hare et al., *Proc. Natl. Acad. Sci. USA*, 78: 1527-1531 (1981); Mulligan & Berg, *Proc. Natl. Acad. Sci. USA*, 78: 2072-2076 (1981); Colberre-Garapin et al., *J. Mol. Biol.*, 150:1-14 (1981); Santerre et al., *Gene*, 30: 147-156 (1984); Kent et al., *Science*, 237: 901-903 (1987); Wigler et al., *Cell*, 11: 223-232 (1977); Szybalska & Szybalski, *Proc. Natl. Acad. Sci. USA*, 48: 2026-2034 (1962); Lowy et al., *Cell*, 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy* 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.), and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, Calif.), and the retroviral vectors pFB-ERV plus pCFB-EGSH from Stratagene (La Jolla, Calif.).

The nucleic acid sequence encoding the immunoglobulin heavy chain polypeptide and the nucleic acid sequence encoding the immunoglobulin light chain polypeptide of the NGF-binding agent can be provided to a cell on the same vector (i.e., in cis). A bi-directional promoter can be used to control expression of both nucleic acid sequences. In another embodiment, a unidirectional promoter can control expression of both nucleic acid sequences. The nucleic acid sequence encoding the immunoglobulin heavy chain polypeptide and the nucleic acid sequence encoding the immunoglobulin light chain polypeptide alternatively can be provided to the population of cells on separate vectors (i.e., in trans). The vector comprising the nucleic acid sequence encoding the immunoglobulin heavy chain polypeptide can comprise the same or different expression control sequences as the vector comprising the nucleic acid sequence encoding the immunoglobulin light chain polypeptide. The separate vectors can be provided to cells simultaneously or sequentially.

The vector(s) comprising the nucleic acid(s) encoding the NGF-binding agent can be introduced into a host cell that is capable of expressing the polypeptides encoded thereby, including any suitable prokaryotic or eukaryotic cell. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas*, *Streptomyces*, *Salmonella*, and *Erwinia*. Particularly useful prokaryotic cells include the various strains of *Escherichia coli* (e.g., K12, HB101 (ATCC No. 33694), DH5α, DH10, MC1061 (ATCC No. 53338), and CC102).

Preferably, the vectors are introduced into a eukaryotic cell. Suitable eukaryotic cells are known in the art and include, for example, yeast cells, insect cells, and mammalian cells. Examples of suitable yeast cells include those from the genera *Kluyveromyces*, *Pichia*, *Rhino-sporidium*, *Saccharomyces*, and *Schizosaccharomyces*. Preferred yeast cells include, for example, *Saccharomyces cerivisae* and *Pichia pastoris*.

Suitable insect cells are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993). Preferred insect cells include Sf-9 and HI5 (Invitrogen, Carlsbad, Calif.).

Preferably, mammalian cells are utilized in the invention. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA,* 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

Most preferably, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS(CRL-1596), Daudi (CCL-213), EB-3 (CCL-85), DT40 (CRL-2111), 18-81 (Jack et al., *Proc. Natl. Acad. Sci. USA,* 85: 1581-1585 (1988)), Raji cells (CCL-86), and derivatives thereof.

A nucleic acid sequence encoding the NGF-binding agent may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols,* Humana Press (1991)); DEAE-dextran; electroporation; cationic liposome-mediated transfection; tungsten particle-facilitated microparticle bombardment (Johnston, *Nature,* 346: 776-777 (1990)); and strontium phosphate DNA co-precipitation (Brash et al., *Mol. Cell. Biol.,* 7: 2031-2034 (1987)). Phage or viral vectors can be introduced into host cells, after growth of infectious particles in suitable packaging cells many of which are commercially available.

The invention provides a composition comprising the isolated immunoglobulin heavy chain polypeptide, the isolated immunoglobulin light chain polypeptide, the isolated NGF-binding agent, or the vector comprising a nucleic acid sequence encoding any of the foregoing. Preferably, the composition is a pharmaceutically acceptable (e.g., physiologically acceptable) composition, which comprises a carrier, preferably a pharmaceutically (e.g., physiologically acceptable) carrier, and the immunoglobulin heavy chain polypeptide, the isolated immunoglobulin light chain polypeptide, or the NGF-binding agent. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., *Remington: The Science and Practice of Pharmacy,* 21$^{st}$ *Edition,* Lippincott Williams & Wilkins, Philadelphia, Pa. (2001).

The invention further provides a method of treating an NGF-mediated disease in a mammal. The method comprises administering the aforementioned composition to a mammal having an NGF-mediated disease, whereupon the NGF-mediated disease is treated in the mammal. The term "NGF-mediated disease," as used herein, refers to any disease or disorder in which the presence of NGF causes or contributes to the pathological effects of the disease, or a decrease in NGF levels or activity has a therapeutic benefit in mammals, preferably humans. Examples of NGF-mediated diseases include, but are not limited to, any condition associated with pain, including all types of acute, chronic, inflammatory, neuropathic and/or post-surgical pain. Clinical conditions associated with pain include, but are not limited to, post-operative pain, dental pain, migraine, headache, neuralgia, pain associated with burn, pain associated with a wound or kidney stone, pain associated with trauma, neuropathic pain, pain associated with musculo-skeletal disorders (e.g., rheumatoid arthritis, osteoarthritis, ankylosing spondylitis, arthropathies, non-articular rheumatism, peri-articular disorders, psoriasis, psoriatic arthritis, and multiple sclerosis), pain associated with inflammatory bowel disease, pain associated with cancer and cancer metastases, peripheral neuropathy, post-herpetic neuralgia, inflammatory pain, pain associated with mucositis, pain associated with dysmenorrheal, pain associated with a sprain, visceral pain, pain associated with ovarian cysts, pain associated with pancreatitis, pain associated with prostatitis, pain associated with cystitis, pain associated with chemical or thermal burns, back pain, lower back pain, pain associated with sciatica, pain associated with osteoarthritis, pain associated with diabetic neuropathy, and abdominal pain.

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the NGF-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the NGF-binding agent to elicit a desired response in the individual. For example, a therapeutically effective amount of an NGF-binding agent of the invention is an amount which decreases NGF bioactivity in a human (e.g., by blocking binding toTrkA).

Alternatively, the pharmacologic and/or physiologic effect may be prophylactic, i.e., the effect completely or partially prevents a disease or symptom thereof. In this respect, the inventive method comprises administering a "prophylactically effective amount" of the NGF-binding agent. A "prophylactically effective amount" refers to an amount effective, at dosages and for periods of time necessary, to achieve a desired prophylactic result (e.g., prevention of disease onset).

A typical dose can be, for example, in the range of 1 pg/kg to 20 mg/kg of animal body weight; however, doses below or above this exemplary range are within the scope of the invention. The daily parenteral dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µg/kg, about 1 mg/kg, about 5 mg/kg, about 10 mg/kg, or a range defined by any two of the foregoing values), preferably from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising the NGF-binding agent of the invention can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive NGF-binding agent can be measured by any suitable method known in the art. For example, the biological activity can be assessed by determining the stability of a particular NGF-binding agent. In one embodiment of the invention, the NGF-binding agent (e.g., an antibody) has an in vivo half life between about six hours and 45 days (e.g., about six hours, about 10 hours, about 12 hours, about 1 day, about 5 days, about 10 days, about 15 days, about 25 days, about 35 days, about 40 days, about 45 days, or a range defined by any two of the foregoing values). In one embodiment, the NGF-binding agent can have an in vivo half life between about 6 hours and 20 days (e.g., about 15 hours, about 20 hours, about 2 days, about 3 days, about 7 days, about 12 days, about 14 days, about 17 days, about 19 days, or a range defined by any two of the foregoing values). In another embodiment, the NGF-binding agent can have an in vivo half life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values). The biological activity of a particular NGF-binding agent also can be assessed by determining its binding affinity to NGF or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 femtomolar (fM) to about 1 millimolar (mM) (e.g., from about 1 picomolar (pM) to about 1 nanomolar (nM), or from about 1 nM to about 1 micromolar (µM)). In one embodiment, the NGF-binding agent can bind to NGF with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the NGF-binding agent can bind to NGF with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), antigen panning, and/or ELISA (see, e.g., Janeway et al. (eds.), *Immunobiology*, 5$^{th}$ ed., Garland Publishing, New York, N.Y., 2001).

The NGF-binding agent of the invention may be administered alone or in combination with other drugs (e.g., as an adjuvant). For example, the NGF binding agent can be administered in combination with other agents for the treatment or prevention of the NGF-mediated diseases disclosed herein. In this respect, the NGF-binding agent can be used in combination with analgesics, anti-depressants, anti-convulsants, anxiolytics, opioids and/or non-steroidal anti-inflammatory drugs (e.g., acetaminophen, ibuprofen, hydrocodone, fentanyl, oxycodone, oxycontin, buprenorphine, pethidine, diamorphine, methadone, pentazocine, dextromoramide, dipipanone, amitriptyline, COX-2 inhibitors, ketoprofen, piroxicam, gabapentin, orphenadrine, cyclobenzaprine, trazodone, clonidine, celecoxib, duloxetine, *cannabis*, pregabalin and axomadol).

In addition to therapeutic uses, the NGF-binding agent described herein can be used in diagnostic or research applications. In this respect, the NGF-binding agent can be used in a method to diagnose an NGF-mediated disease or disorder. In a similar manner, the NGF-binding agent can be used in an assay to monitor NGF levels in a subject being tested for an NGF-associated disease or disorder. Research applications include, for example, methods that utilize the NGF-binding agent and a label to detect NGF in a sample, e.g., in a human body fluid or in a cell or tissue extract. The NGF-binding agent can be used with or without modification, such as covalent or non-covalent labeling with a detectable moiety. For example, the detectable moiety can be a radioisotope (e.g., $^3$H, $^{14}$C, $^{32}$P, $^{35}$S, or $^{125}$I), a fluorescent or chemiluminescent compound (e.g., fluorescein isothiocyanate, rhodamine, or luciferin), or an enzyme (e.g., alkaline phosphatase, beta-galactosidase, or horseradish peroxidase). Any method known in the art for separately conjugating an antigen-binding agent (e.g., an antibody) to a detectable moiety may be employed in the context of the invention (see, e.g., Hunter et al., *Nature*, 194: 495-496 (1962); David et al., *Biochemistry*, 13: 1014-1021 (1974); Pain et al., *J. Immunol. Meth.*, 40: 219-230 (1981); and Nygren, *J. Histochem. and Cytochem.*, 30: 407-412 (1982)).

NGF levels can be measured using the inventive NGF-binding agent by any suitable method known in the art. Such methods include, for example, ELISA, radioimmunoassay (RIA), and FACS. Normal or standard expression values of NGF can be established using any suitable technique, e.g., by combining a sample comprising, or suspected of comprising, an NGF polypeptide with an NGF-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of NGF polypeptide expressed in a sample is then compared with the standard values.

The NGF-binding agent can be provided in a kit, i.e., a packaged combination of reagents in predetermined amounts with instructions for performing a diagnostic assay. If the NGF-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following example further illustrates the invention but, of course, should not be construed as in any way limiting its scope.

EXAMPLE

This example demonstrates a method of generating a Nerve Growth Factor (NGF)-binding agent.

A fully human library of IgGs directed against human βNGF was generated, and was based on germline sequence variable (V)-gene segments joined to pre-recombined (D)J regions isolated from a panel of human donors. A total of nine heavy chain (HC) and nine light chain (LC) (5κ and 4λ) human germline V-gene segments were selected for the library based on the frequency of in vivo germline usage (see, e.g., Glanville J, et al., *Proc. Natl. Acad. Sci. USA*, 106: 20216-20221 (2009)); and Knappik A, et al., *J. Mol. Biol.*, 296: 57-86 (2000)). V regions were chemically synthesized and fused to (D)J region sequences (encoding CDR3 and FR4 diversity) isolated by PCR from pooled peripheral blood mononuclear cells (PBMCs) of normal donors. Full-length V regions for HC and LC were assembled with human HC and LC constant regions and transfected into HEK293 cells. A sampling of the stably selected library by high-throughput sequencing (HTP) provided a lower estimate of $6 \times 10^7$ total diversity of combinatorially-expressed antibody sequences (see, e.g., Weinstein et al., *Science*, 324: 807-810 (2009)). The library was designed to provide multiple initial candidates with germline V-gene segments for further maturation by somatic hypermuation (SHM).

The transfected library was expanded to $10^9$ cells, and subjected to four rounds of negative selection against streptavidin (SA)-coupled magnetic beads, followed by a single round of positive selection against SA-coupled magnetic beads coated with biotinylated βNGF. Positively selected cells were expanded, and two rounds of fluorescence-activated cell sorting (FACS) selection were performed under high avidity conditions. Single cell clones (SCCs) were isolated with the second round of FACS selection, sequenced, and each clone was characterized for binding to βNGF and the ability of soluble TrkA-Fc receptor to compete for this binding. Of 37 SCCs isolated from round 2, six unique clones were chosen for affinity maturation and stably transfected with AID. Three rounds of FACS selection were performed using progressively lower concentrations of fluorescently labeled hβNGF antigen. Selected antibody-expressing cells exhibited improved hβNGF binding by the third round of SHM, and HC and LC sequencing of each selected population revealed enriched mutations, contained primarily in HC CDR regions.

Expression in the HEK293 cells was stably maintained using an episomal system that supports a low copy number (3-5 per cell) of each vector (see, e.g., Horlick et al., *Gene*, 243: 187-194 (2000)). Unique HC and LCs from each SCC were cloned, combinatorially paired, expressed in HEK293 cells, and assessed in Biacore and flow cytometry-based antigen-binding assays. The HC/LC pair from each SCC providing the best binding to βNGF were retransfected with AID for further maturation. The sole HC isolated from SCC C10A (SEQ ID NO: 15) contained an enriched mutation, S31N, in CDR1. One of three distinct germline LC sequences recovered from SCC C10A (SEQ ID NO: 30), in combination with this HC, was used for further maturation. The resulting HC/LC pair was denoted APE391. Affinity maturation of APE391 was carried out utilizing two independent but initially identical cell populations, denoted strategies 51 and S2. Rounds 1-3 of FACS selection for each strategy were performed using low nM concentrations of βNGF fused to wasabi fluorescent protein (WFP), with each round selecting approximately 0.2-0.5% of the brightest cells. Subsequent rounds of FACS selection used low pM concentrations of fluorochrome-labeled βNGF in combination with unlabeled βNGF competition. Sequences were monitored by the sequencing of approximately 40 HC and LC after each round. HTP sequencing was also employed to monitor enriching mutations during early rounds of FACS selection of strategy S1. Affinity maturation was observed starting with the third round of FACS selection, continuing through the final rounds of affinity maturation (Round 12 for S1, Round 9 for S2), as evidenced by improved βNGF binding, sequence data as reported in Table 3 and Table 4, and Biacore analysis of isolated clones.

TABLE 3

| SHM Strategy | Starting Sequence | Ending Sequence | Start NA | End NA | Mutation |
|---|---|---|---|---|---|
| S2 | AGGCT | AGGGT | C | G | A24G |
| S1, S2 | AGGCT | AGCCT | G | C | A24P |
| S1 | TGCTA | TGTTA | C | T | A33V |
| S1 | TGATT | TGCTT | A | C | D100A |
| S2 | TGATT | TGGTT | A | G | D100G |

TABLE 3-continued

| SHM Strategy | Starting Sequence | Ending Sequence | Start NA | End NA | Mutation |
|---|---|---|---|---|---|
| S2 | AGGGC | AAGAC, AAGGC | G | A | G44R |
| S2 | TGGTA | TGATA | G | A | G55D |
| S1 | GGGCA | GGACA | G | A | G65D |
| S1, S2 | GGCTT | GGTTT | C | T | L45F |
| S1 | CAAAC | CACAC | A | C | N58H |
| S1, S2 | ATCGT | ATAGT | C | A | R100gS |
| S1 | CAGCA | CATCA | G | T | S30I |
| S1, S2 | CAGCA | CAACA | G | A | S30N |
| S1, S2 | CAGCT | CAACT | G | A | S31N |
| S1, S2 | CAGCT | CAACT | G | A | S35N |
| S1, S2 | GAGCA | GAACA | G | A | S76N |
| S2 | GGGTG | GGCTG | G | C | V37L |
| S1 | ATGCT | ATATT | G, C | A, T | GDTFSNYI (SEQ ID NO: 34) |
| S2 | AGGCTT | AGGCGGCTT | | | A (24) |
| S1 | CTGGAGGCACCTTCAGCAACTATGCTATC (SEQ ID NO: 35) | CTGGAGGCACCTTCAGCAACTATGCTATCACCTTCAGCAACTATGCTATC (SEQ ID NO: 36) | | | TFSNYAI (28) (SEQ ID NO: 37) |
| S1 | CTGGAGGCACCTTCAGCAACTATGCTATC (SEQ ID NO: 38) | CTGGAGACACCTTCAGCAACTATGCTACTGGAGACACCTTCAGCAACTATGCTATC (SEQ ID NO: 39) | | | GDTFSNYA (26) (SEQ ID NO: 40) |
| S2 | CAGGTGCAGCTGGGTTCAGTCTGGGGCTGAGGTGAAGAAGCCTGGGT (SEQ ID NO: 41) | CAGGTGCAGCTGGTTCAGTCTGGGGCTGAGGTGAACTGGGTGCAGCTGGTTCAGTCTGGGGCTGAGGTGAAGAA (SEQ ID NO: 42) | | | NWVQLVASGQEV (12) (SEQ ID NO: 43) |

All HC mutations and insertion events observed during the S1 and S2 evolution strategy are shown.
The first column indicates the strategy in which the mutation/insertion was identified (S1 or S2).
The second and third columns show the starting and ending nucleotide sequence surrounding the site of mutation (mutation underlined) or insertion (duplicated sequence underlined).
Column 5 through 7 highlight the starting and ending nucleotide and resulting amino acid substitution (referenced by Kabat numbering). Seven of the 19 mutations involved nucleotide transversions, while the remaining 12 involved nucleotide transitions. Sixteen of the 19 mutations were initiated at the nucleotides G or C, three at nucleotide A, and thirteen of 19 occurred at known AID hotspots (WRCH) located primarily within CDRs 1, 2, or 3.

TABLE 4

| SHM Event | SHM Strategy | Starting Sequence | Ending Sequence | Start NA | End NA | Mutation | Fold Enrichment |
|---|---|---|---|---|---|---|---|
| Mutation | S1 | TGGTT | TGGGT, TGCTT | T, G | G, C | V5GL | 18.8, 11.4 |
| Mutation | S1 | TGCTA | TGGTA, TGTTA | C | G, T | A33GV | 15.4, 9.4 |
| Mutation | S1 | CAGCA | CAACA, CACCA | G | A, C | S30NT | 8.7, 6.9 |

TABLE 4-continued

| SHM Event | SHM Strategy | Starting Sequence | Ending Sequence | Start NA | End NA | Mutation | Fold Enrichment |
|---|---|---|---|---|---|---|---|
| Mutation | S1 | GGCTT | GGTTT | C | T | L45F | 11.9 |
| Mutation | S1 | TGGTA | TGATA, TTGTA, TGCTA | G | A, C, T | G55DCA | 7.0, 36.6, 14.0 |
| Mutation | S1 | AAACT | AAAGT, AAGCT | C, A | G | N58KS | 4.2, 12.5 |
| Mutation | S1 | GAGCA | GAACA, GACCA, GAGAA | G | A, C | S76NTR | 3.7, 21.2, 8.0 |
| Mutation | S1 | CCGTG | CCCTG | G | C | V89L | 15.9 |
| Mutation | S1 | TCGTT | TCCTT | G | C | R100gP | 37.3 |
| Mutation | S1 | CAGCT | CACCT, CAGGT | G, C | C, G | S35TR | 6.5, 16.8 |
| Mutation | S1 | GGGCA | GGTCA | G | T | G65V | 7.3 |

All HC mutations and insertion events observed by high-throughput sequencing during the S1 evolution strategy are shown.
The first column indicates the category of SHM event (mutation or insertion/deletion) and the second column indicates the strategy in which it was identified (S1 or S2).
The third and fourth columns show the starting and ending nucleotide sequence surrounding the site of mutation (mutation underlined).
Column 5 through 7 highlight the starting and ending nucleotide and resulting amino acid substitution (referenced by Kabat numbering).
The final column shows the fold increase in the nucleotide mutation frequency from rounds 1 to 3.

Maturation of APE391 in strategy S1 continued with the observation of an L45F mutation in the HC in round 3 (out of 32 sequences) (SEQ ID NO: 16), with all recovered sequences containing this mutation by round 4. This resulting HC/LC pair (i.e., SEQ ID NO: 16 and SEQ ID NO: 30, respectively) was denoted APE583. Kinetic characterization of this mutation was associated with a significant improvement in binding affinity for hβNGF. Two HC FW1/CDR1 insertions, resulting in HC sequences having SEQ ID NO: 21 and SEQ ID NO: 20, respectively, were found to be enriched in the context of APE583 to a majority of recovered sequences from rounds 6 and 7 (HC/LC pairs denoted APE659 and APE646, respectively). Each insertion mutant was associated with an approximately 20-fold improvement in binding affinity. An HC CDR3 mutation, D100A, was observed in round 12 in the context of the APE646 variant (SEQ ID NO: 23), which improved $k_{on}$ 100-fold and lead to an affinity of 760 pM. This HC/LC pair was denoted APE803, and contained an HC comprising SEQ ID NO: 23, and an LC comprising SEQ ID NO: 31.

Affinity maturation of APE391 in the S2 strategy commenced in the HC with the incorporation of a single amino acid insertion, A24 (SEQ ID NO: 17, denoted APE608 when paired with a LC comprising SEQ ID NO: 30), coincident with incorporation of mutations G44R and G55D in round 3, each associated with significant improvements in affinity. APE608 became the predominate HC sequence by round 5, with additional CDR1, FW3 and CDR3HC mutations, identified in subsequent rounds. L45F, identified early in the S1 evolution strategy, was not observed in strategy S2 until round 10 of affinity maturation. Other affinity maturation events in the S1 strategy, such as D100A and the longer CDR1 codon insertions, were not detected in the S2 strategy.

Sequence analysis identified a total of 18 enriched mutations within the HC that improved antigen-binding kinetics, which are set forth in Table 3. Seven of the 18 enriched mutations were observed in both S1 and S2 strategies; five of the remaining mutations involved sequence changes at the same amino acid positions (e.g., D100A vs. D100G) and were also found in both S1 and S2 strategies. Eleven substitutions were cataloged early in the S1 strategy, nine of which were identical or related to those observed in later rounds. Enriching mutations were also identified by HTP sequencing of the LC, one of which (A60T—SEQ ID NO: 31) was incorporated into the affinity matured antibodies denoted APE925 (HC comprising SEQ ID NO: 28) and denoted APE928 (HC comprising SEQ ID NO: 29). Four independent AID-mediated codon insertions were observed in the maturing HC sequence near the junction of FW1 and CDR1 (see Table 3), with insertions ranging from a single alanine to segments containing 7, 8, and 12 amino acids. All four insertions originate from local sequence duplications, three of the four contained secondary AID mutations in combination with the insertion, and each was associated with a significant improvement in binding affinity for the antigen, all of which are hallmarks of insertions observed in in vivo-derived antibodies (see, e.g., Krause et al., *MBio,* 2: e00345-10 (2011); Miura et al., *Mol. Med.,* 9: 166-174 (2003); and We et al., *Science,* 333: 1593-1602 (2011)).

Mutations observed in both strategies not utilized by APE803 were recombined by overlap extension PCR in a combinatorial library, each HC/LC pair was expressed and characterized on Biacore utilizing direct capture of secreted antibodies. Variants identified with dissociation constants in the low pM range were further characterized in Biacore experiments utilizing normalized concentrations of purified antibodies captured at low densities ($R_{max}$<30), with APE925 possessing a KD of 25 pM.

Antibodies spanning the S1 affinity maturation trajectory were characterized for their ability to (a) antagonize binding of βNGF to TrkA, (b) compete for binding to βNGF with known anti-βNGF antibodies, and (c) inhibit βNGF-dependent TrkA signaling in a rat pheochromocytoma-derived cell line (PC12). C10A-derived antibodies demonstrated a dose-dependent ability to inhibit binding of an anti-βNGF antibody (Tanezumab—Pfizer, New York, N.Y.) to βNGF in a homogenous time-resolved fluorescence (HTRF) assay that correlated well with kinetic characterization of each clone. Antibodies APE925 and APE928 demonstrated a dose-dependent inhibition of TrkA-Fc binding to βNGF and inhibited βNGF-induced TrkA signaling and activation of extracellular regulated kinase (ERK)1/2 in PC12 cells.

The results of this example demonstrate that the inventive NGF-binding agent can bind βNGF with low pM dissociation constants and exhibit potent and functional inhibition of βNGF binding to its cognate receptor.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated Nerve Growth Factor (NGF)-binding agent comprising an immunoglobulin heavy chain polypeptide comprising SEQ ID NO: 29, and an immunoglobulin light chain polypeptide comprising SEQ ID NO: 31, wherein the NGF binding agent is an antibody, an antibody conjugate, or an antigen-binding fragment thereof.

2. A composition comprising the isolated NGF-binding agent of claim 1 and a pharmaceutically acceptable carrier.

* * * * *

SEQUENCE LISTING

```
<160> NUMBER OF SEQ ID NOS: 43

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Phe Ser Leu Thr Asn Asn Asn Val Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Gly Val Trp Ala Gly Gly Ala Thr Asp Tyr Asn Ser Ala Leu Lys Ser
1               5                   10                  15

<210> SEQ ID NO 3
<211> LENGTH: 121
<212> TYPE: PRT
<213> ORGANISM: Artificial Sequence
<220> FEATURE:
<223> OTHER INFORMATION: Synthetic

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Asn Thr Tyr
            20                  25                  30
```

```
Ser Met Asn Trp Val Arg Gln Ala Pro Gly Lys Gly Leu Glu Trp Val
            35                  40                  45

Ser Val Ile Ser Thr Gly Gly Thr Arg Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Tyr Ser Ser Thr Leu Tyr Ala Met Asp Ala
                100                 105                 110

Trp Gly Gln Gly Thr Leu Val Thr Val
            115                 120

<210> SEQ ID NO 4
<211> LENGTH: 121
<212> TYPE: PRT
<213> ORGANISM: Artificial Sequence
<220> FEATURE:
<223> OTHER INFORMATION: Synthetic

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Thr Tyr
            20                  25                  30

Asn Met Asn Trp Val Arg Gln Ala Pro Gly Lys Gly Leu Glu Trp Val
            35                  40                  45

Ser Val Ile Ser Thr Gly Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Tyr Ser Ser Ser Thr Leu Tyr Ala Met Asp Ala
                100                 105                 110

Trp Gly Gln Gly Thr Thr Val Thr Val
            115                 120

<210> SEQ ID NO 5
<211> LENGTH: 121
<212> TYPE: PRT
<213> ORGANISM: Artificial Sequence
<220> FEATURE:
<223> OTHER INFORMATION: Synthetic

<400> SEQUENCE: 5

Lys Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Thr Tyr
            20                  25                  30

Asn Met Asn Trp Val Arg Gln Ala Pro Gly Lys Gly Leu Asp Trp Val
            35                  40                  45

Ser Val Ile Ser Thr Gly Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Gly Gly Tyr Ser Ser Thr Leu Tyr Ala Met Asp Ala
            100                 105                 110

Trp Gly Gln Gly Thr Thr Val Thr Val
        115                 120

<210> SEQ ID NO 6
<211> LENGTH: 121
<212> TYPE: PRT
<213> ORGANISM: Artificial Sequence
<220> FEATURE:
<223> OTHER INFORMATION: Synthetic

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Thr Tyr
            20                  25                  30

Asn Met Asn Trp Val Arg Gln Ala Pro Gly Lys Gly Leu Glu Trp Val
        35                  40                  45

Ser Val Ile Ser Thr Gly Gly Ser Asn Thr Tyr Tyr Ala Tyr Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Tyr Ser Ser Thr Leu Tyr Ala Met Asp Ala
            100                 105                 110

Trp Gly Gln Gly Thr Thr Val Thr Val
        115                 120

<210> SEQ ID NO 7
<211> LENGTH: 108
<212> TYPE: PRT
<213> ORGANISM: Artificial Sequence
<220> FEATURE:
<223> OTHER INFORMATION: Synthetic

<400> SEQUENCE: 7

Asp Ile Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile Tyr Asn Ala
            20                  25                  30

Leu Ala Trp Tyr Gln Gln Lys Pro Gly Lys Ser Pro Gln Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln His Tyr Phe Gly Tyr Pro Arg
                85                  90                  95

Thr Phe Gly Gly Gly Thr Lys Leu Glu Leu Lys Arg
            100                 105

<210> SEQ ID NO 8
<211> LENGTH: 108
<212> TYPE: PRT
<213> ORGANISM: Artificial Sequence
<220> FEATURE:
<223> OTHER INFORMATION: Synthetic
```

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln His Tyr Phe Asp Tyr Pro Arg
                85                  90                  95

Thr Phe Gly Gln Gly Thr Lys Val Glu Ile Lys Arg
            100                 105

<210> SEQ ID NO 9
<211> LENGTH: 108
<212> TYPE: PRT
<213> ORGANISM: Artificial Sequence
<220> FEATURE:
<223> OTHER INFORMATION: Synthetic

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Ala
            20                  25                  30

Leu Ala Trp Tyr Gln Gln Lys Pro Gly Lys Val Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Tyr Phe Gly Tyr Pro Arg
                85                  90                  95

Thr Phe Gly Gln Gly Thr Lys Val Glu Ile Lys Arg
            100                 105

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Ala
            20                  25                  30

Leu Ala Trp Tyr Gln Gln Lys Pro Gly Lys Val Pro Lys Leu Leu Ile
        35                  40                  45

Tyr Asn Thr Asp Thr Leu His Thr Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Phe Asp Tyr Pro Arg
                85                  90                  95

Thr Phe Gly Gln Gly Thr Lys Val Glu Ile Lys Arg
            100                 105

<210> SEQ ID NO 11
<211> LENGTH: 108
<212> TYPE: PRT
<213> ORGANISM: Artificial Sequence
<220> FEATURE:
<223> OTHER INFORMATION: Synthetic

<400> SEQUENCE: 11

Asp Ile Gln Met Thr Gln Ser Pro Ser Ser Leu Ser Ala Ser Val Gly
1               5                   10                  15

Asn Arg Val Thr Ile Thr Cys Arg Ala Ser Glu Asp Ile Tyr Asn Ala
            20                  25                  30

Leu Ala Trp Tyr Gln Gln Lys Pro Gly Lys Val Pro Lys Leu Leu Ile
        35                  40                  45

Tyr Asn Thr Asp Thr Leu His Thr Gly Val Pro Ser Arg Phe Ser Gly
    50                  55                  60

Ser Glu Ser Gly Thr Asp Leu Thr Leu Thr Ile Ser Ser Leu Gln Pro
65                  70                  75                  80

Glu Asp Val Ala Thr Tyr Tyr Cys Gln Gln Tyr Phe Asp Tyr Pro Arg
                85                  90                  95

Thr Phe Gly Gln Gly Thr Lys Val Glu Ile Lys Arg
            100                 105

<210> SEQ ID NO 12
<211> LENGTH: 108
<212> TYPE: PRT
<213> ORGANISM: Artificial Sequence
<220> FEATURE:
<223> OTHER INFORMATION: Synthetic

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Ala
            20                  25                  30

Leu Ala Trp Tyr Gln Gln Lys Pro Gly Lys Val Pro Lys Leu Leu Ile
        35                  40                  45

Tyr Asn Thr Asp Arg Leu His Thr Gly Val Pro Ser Arg Phe Ser Gly
    50                  55                  60

Ser Glu Ser Gly Thr Asp Leu Thr Leu Thr Ile Ser Ser Leu Gln Pro
65                  70                  75                  80

Glu Asp Val Ala Thr Tyr Tyr Cys Gln Gln Tyr Phe Asp Tyr Pro Arg
                85                  90                  95

Thr Phe Gly Gln Gly Thr Lys Val Glu Ile Lys Arg
            100                 105

<210> SEQ ID NO 13
<211> LENGTH: 108
<212> TYPE: PRT
<213> ORGANISM: Artificial Sequence
<220> FEATURE:
<223> OTHER INFORMATION: Synthetic

<400> SEQUENCE: 13

```
Asp Ile Gln Met Thr Gln Ser Pro Ser Ser Leu Ser Ala Ser Val Gly
1               5                   10                  15

Asn Arg Val Thr Ile Thr Cys Arg Ala Ser Glu Asp Ile Tyr Asn Ala
            20                  25                  30

Leu Ala Trp Tyr Gln Gln Lys Pro Gly Lys Val Pro Lys Leu Leu Ile
        35                  40                  45

Tyr Asn Thr Asp Thr Leu His Thr Gly Val Pro Ser Arg Phe Ser Gly
50                  55                  60

Ser Glu Ser Gly Thr Asp Leu Thr Leu Thr Ile Ser Ser Leu Gln Pro
65                  70                  75                  80

Glu Asp Val Ala Thr Tyr Tyr Cys Gln Gln Tyr Phe Asp Tyr Pro Arg
                85                  90                  95

Thr Phe Gly Gln Gly Thr Lys Val Glu Ile Lys Arg
            100                 105
```

<210> SEQ ID NO 14
<211> LENGTH: 126
<212> TYPE: PRT
<213> ORGANISM: Artificial Sequence
<220> FEATURE:
<223> OTHER INFORMATION: Synthetic

<400> SEQUENCE: 14

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Glu Tyr Tyr Asp Tyr Val Trp Gly Ser Tyr Arg Tyr
            100                 105                 110

Asn Tyr Phe Asp Tyr Trp Gly Gln Gly Thr Leu Val Thr Val
        115                 120                 125
```

<210> SEQ ID NO 15
<211> LENGTH: 126
<212> TYPE: PRT
<213> ORGANISM: Artificial Sequence
<220> FEATURE:
<223> OTHER INFORMATION: Synthetic

<400> SEQUENCE: 15

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Pro Glu Tyr Tyr Asp Tyr Val Trp Gly Ser Tyr Arg Tyr
            100                 105                 110

Asn Tyr Phe Asp Tyr Trp Gly Gln Gly Thr Leu Val Thr Val
        115                 120                 125
```

<210> SEQ ID NO 16
<211> LENGTH: 126
<212> TYPE: PRT
<213> ORGANISM: Artificial Sequence
<220> FEATURE:
<223> OTHER INFORMATION: Synthetic

<400> SEQUENCE: 16

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Phe Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Glu Tyr Tyr Asp Tyr Val Trp Gly Ser Tyr Arg Tyr
            100                 105                 110

Asn Tyr Phe Asp Tyr Trp Gly Gln Gly Thr Leu Val Thr Val
        115                 120                 125
```

<210> SEQ ID NO 17
<211> LENGTH: 127
<212> TYPE: PRT
<213> ORGANISM: Artificial Sequence
<220> FEATURE:
<223> OTHER INFORMATION: Synthetic

<400> SEQUENCE: 17

```
Gln Val Gln Leu Val Gln Ser Gly Ala Glu Val Lys Lys Pro Gly Ser
1               5                   10                  15

Ser Val Lys Val Ser Cys Lys Ala Ala Ser Gly Gly Thr Phe Ser Asn
            20                  25                  30

Tyr Ala Ile Ser Trp Val Arg Gln Ala Pro Gly Gln Gly Leu Glu Trp
        35                  40                  45

Met Gly Gly Ile Ile Pro Ile Phe Gly Thr Ala Asn Tyr Ala Gln Lys
    50                  55                  60

Phe Gln Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Gly Pro Glu Tyr Tyr Asp Tyr Val Trp Gly Ser Tyr Arg
            100                 105                 110

Tyr Asn Tyr Phe Asp Tyr Trp Gly Gln Gly Thr Leu Val Thr Val
        115                 120                 125
```

-continued

```
<210> SEQ ID NO 18
<211> LENGTH: 126
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Pro Ser Gly Gly Thr Phe Asn Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Glu Tyr Tyr Asp Tyr Val Trp Gly Ser Tyr Arg Tyr
            100                 105                 110

Asn Tyr Phe Asp Tyr Trp Gly Gln Gly Thr Leu Val Thr Val
        115                 120                 125

<210> SEQ ID NO 19
<211> LENGTH: 126
<212> TYPE: PRT
<213> ORGANISM: Artificial Sequence
<220> FEATURE:
<223> OTHER INFORMATION: Synthetic

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ile Asn Tyr
            20                  25                  30

Ala Ile Ser Trp Val Arg Gln Ala Pro Gly Gln Arg Leu Glu Trp Met
        35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Glu Tyr Tyr Asp Tyr Val Trp Gly Ser Tyr Arg Tyr
            100                 105                 110

Asn Tyr Phe Asp Tyr Trp Gly Gln Gly Thr Leu Val Thr Val
        115                 120                 125

<210> SEQ ID NO 20
<211> LENGTH: 133
<212> TYPE: PRT
<213> ORGANISM: Artificial Sequence
<220> FEATURE:
<223> OTHER INFORMATION: Synthetic

<400> SEQUENCE: 20

Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Gly Thr Phe Ser Asn Tyr
            20                  25                  30

Ala Ile Thr Phe Ser Asn Tyr Ala Ile Ser Trp Val Arg Gln Ala Pro
        35                  40                  45

Gly Gln Gly Phe Glu Trp Met Gly Gly Ile Ile Pro Ile Phe Gly Thr
    50                  55                  60

Ala Asn Tyr Ala Gln Lys Phe Gln Gly Arg Val Thr Ile Thr Ala Asp
65                  70                  75                  80

Glu Ser Thr Ser Thr Ala Tyr Met Glu Leu Ser Ser Leu Arg Ser Glu
                85                  90                  95

Asp Thr Ala Val Tyr Tyr Cys Ala Arg Gly Pro Glu Tyr Tyr Asp Tyr
            100                 105                 110

Val Trp Gly Ser Tyr Arg Tyr Asn Tyr Phe Asp Tyr Trp Gly Gln Gly
        115                 120                 125

Thr Leu Val Thr Val
    130

<210> SEQ ID NO 21
<211> LENGTH: 135
<212> TYPE: PRT
<213> ORGANISM: Artificial Sequence
<220> FEATURE:
<223> OTHER INFORMATION: Synthetic

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Asn Tyr
            20                  25                  30

Ala Thr Gly Asp Thr Phe Ser Asn Tyr Ala Ile Ser Trp Val Arg Gln
        35                  40                  45

Ala Pro Gly Gln Gly Phe Glu Trp Met Gly Gly Ile Ile Pro Ile Phe
    50                  55                  60

Gly Thr Ala Asn Tyr Ala Gln Lys Phe Gln Gly Arg Val Thr Ile Thr
65                  70                  75                  80

Ala Asp Glu Ser Thr Ser Thr Ala Tyr Met Glu Leu Ser Ser Leu Arg
                85                  90                  95

Ser Glu Asp Thr Ala Val Tyr Tyr Cys Ala Arg Gly Pro Glu Tyr Tyr
            100                 105                 110

Asp Tyr Val Trp Gly Ser Tyr Arg Tyr Asn Tyr Phe Asp Tyr Trp Gly
        115                 120                 125

Gln Gly Thr Leu Val Thr Val
    130                 135

<210> SEQ ID NO 22
<211> LENGTH: 133
<212> TYPE: PRT
<213> ORGANISM: Artificial Sequence
<220> FEATURE:
<223> OTHER INFORMATION: Synthetic

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Phe Ser Asn Tyr Ala Ile Ser Trp Val Arg Gln Ala Pro
```

```
                    35                  40                  45
Gly Gln Gly Leu Glu Trp Met Gly Gly Ile Ile Pro Ile Phe Gly Thr
        50                  55                  60
Ala Asn Tyr Ala Gln Lys Phe Gln Gly Arg Val Thr Ile Thr Ala Asp
65                  70                  75                  80
Glu Ser Thr Ser Thr Ala Tyr Met Glu Leu Ser Ser Leu Arg Ser Glu
                85                  90                  95
Asp Thr Ala Val Tyr Tyr Cys Ala Arg Gly Pro Glu Tyr Tyr Asp Tyr
            100                 105                 110
Val Trp Gly Ser Tyr Arg Tyr Asn Tyr Phe Asp Tyr Trp Gly Gln Gly
        115                 120                 125
Thr Leu Val Thr Val
        130

<210> SEQ ID NO 23
<211> LENGTH: 135
<212> TYPE: PRT
<213> ORGANISM: Artificial Sequence
<220> FEATURE:
<223> OTHER INFORMATION: Synthetic

<400> SEQUENCE: 23

Gln Val Gln Leu Val Gln Ser Gly Ala Glu Val Lys Lys Pro Gly Ser
1               5                   10                  15
Ser Val Lys Val Ser Cys Lys Ala Ser Gly Asp Thr Phe Ser Asn Tyr
            20                  25                  30
Ala Thr Gly Asp Thr Phe Ser Asn Tyr Ala Ile Ser Trp Val Arg Gln
        35                  40                  45
Ala Pro Gly Gln Gly Phe Glu Trp Met Gly Gly Ile Ile Pro Ile Phe
    50                  55                  60
Gly Thr Ala Asn Tyr Ala Gln Lys Phe Gln Gly Arg Val Thr Ile Thr
65                  70                  75                  80
Ala Asp Glu Ser Thr Ser Thr Ala Tyr Met Glu Leu Ser Ser Leu Arg
                85                  90                  95
Ser Glu Asp Thr Ala Val Tyr Tyr Cys Ala Arg Gly Pro Glu Tyr Tyr
            100                 105                 110
Ala Tyr Val Trp Gly Ser Tyr Arg Tyr Asn Tyr Phe Asp Tyr Trp Gly
        115                 120                 125
Gln Gly Thr Leu Val Thr Val
    130                 135

<210> SEQ ID NO 24
<211> LENGTH: 135
<212> TYPE: PRT
<213> ORGANISM: Artificial Sequence
<220> FEATURE:
<223> OTHER INFORMATION: Synthetic

<400> SEQUENCE: 24

Gln Val Gln Leu Val Gln Ser Gly Ala Glu Val Lys Lys Pro Gly Ser
1               5                   10                  15
Ser Val Lys Val Ser Cys Lys Ala Ser Gly Asp Thr Phe Ser Asn Tyr
            20                  25                  30
Ala Thr Gly Asp Thr Phe Ser Asn Tyr Ala Ile Ser Trp Val Arg Gln
        35                  40                  45
Ala Pro Gly Gln Arg Phe Glu Trp Met Gly Gly Ile Ile Pro Ile Phe
    50                  55                  60
```

Gly Thr Ala Asn Tyr Ala Gln Lys Phe Gln Gly Arg Val Thr Ile Thr
65                  70                  75                  80

Ala Asp Glu Ser Thr Ser Thr Ala Tyr Met Glu Leu Ser Ser Leu Arg
                85                  90                  95

Ser Glu Asp Thr Ala Val Tyr Tyr Cys Ala Arg Gly Pro Glu Tyr Tyr
            100                 105                 110

Ala Tyr Val Trp Gly Ser Tyr Arg Tyr Asn Tyr Phe Asp Tyr Trp Gly
        115                 120                 125

Gln Gly Thr Leu Val Thr Val
    130                 135

<210> SEQ ID NO 25
<211> LENGTH: 135
<212> TYPE: PRT
<213> ORGANISM: Artificial Sequence
<220> FEATURE:
<223> OTHER INFORMATION: Synthetic

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Asn Tyr
            20                  25                  30

Ala Thr Gly Asp Thr Phe Ser Asn Tyr Ala Ile Ser Trp Val Arg Gln
        35                  40                  45

Ala Pro Gly Gln Arg Phe Glu Trp Met Gly Gly Ile Ile Pro Ile Phe
    50                  55                  60

Gly Thr Ala Asn Tyr Ala Gln Lys Phe Gln Gly Arg Val Thr Ile Thr
65                  70                  75                  80

Ala Asp Glu Ser Thr Asn Thr Ala Tyr Met Glu Leu Ser Ser Leu Arg
                85                  90                  95

Ser Glu Asp Thr Ala Val Tyr Tyr Cys Ala Arg Gly Pro Glu Tyr Tyr
            100                 105                 110

Ala Tyr Val Trp Gly Ser Tyr Ser Tyr Asn Tyr Phe Asp Tyr Trp Gly
        115                 120                 125

Gln Gly Thr Leu Val Thr Val
    130                 135

<210> SEQ ID NO 26
<211> LENGTH: 135
<212> TYPE: PRT
<213> ORGANISM: Artificial Sequence
<220> FEATURE:
<223> OTHER INFORMATION: Synthetic

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Asn Asn Tyr
            20                  25                  30

Ala Thr Gly Asp Thr Phe Ser Asn Tyr Ala Ile Asn Trp Val Arg Gln
        35                  40                  45

Ala Pro Gly Gln Arg Phe Glu Trp Met Gly Gly Ile Ile Pro Ile Phe
    50                  55                  60

Asp Thr Ala Asn Tyr Ala Gln Lys Phe Gln Gly Arg Val Thr Ile Thr
65                  70                  75                  80

Ala Asp Glu Ser Thr Asn Thr Ala Tyr Met Glu Leu Ser Ser Leu Arg
                85                  90                  95

-continued

Ser Glu Asp Thr Ala Val Tyr Tyr Cys Ala Arg Gly Pro Glu Tyr Tyr
                100                 105                 110

Ala Tyr Val Trp Gly Ser Tyr Ser Tyr Asn Tyr Phe Asp Tyr Trp Gly
            115                 120                 125

Gln Gly Thr Leu Val Thr Val
        130                 135

<210> SEQ ID NO 27
<211> LENGTH: 135
<212> TYPE: PRT
<213> ORGANISM: Artificial Sequence
<220> FEATURE:
<223> OTHER INFORMATION: Synthetic

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Asn Asn Tyr
            20                  25                  30

Ala Thr Gly Asp Thr Phe Ser Asn Tyr Ala Ile Ser Trp Val Arg Gln
        35                  40                  45

Ala Pro Gly Gln Gly Phe Glu Trp Met Gly Gly Ile Ile Pro Ile Phe
    50                  55                  60

Asp Thr Ala Asn Tyr Ala Gln Lys Phe Gln Gly Arg Val Thr Ile Thr
65                  70                  75                  80

Ala Asp Glu Ser Thr Asn Thr Ala Tyr Met Glu Leu Ser Ser Leu Arg
                85                  90                  95

Ser Glu Asp Thr Ala Val Tyr Tyr Cys Ala Arg Gly Pro Glu Tyr Tyr
                100                 105                 110

Ala Tyr Val Trp Gly Ser Tyr Arg Tyr Asn Tyr Phe Asp Tyr Trp Gly
            115                 120                 125

Gln Gly Thr Leu Val Thr Val
        130                 135

<210> SEQ ID NO 28
<211> LENGTH: 135
<212> TYPE: PRT
<213> ORGANISM: Artificial Sequence
<220> FEATURE:
<223> OTHER INFORMATION: Synthetic

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Asn Asn Tyr
            20                  25                  30

Ala Thr Gly Asp Thr Phe Ser Asn Tyr Ala Ile Ser Trp Val Arg Gln
        35                  40                  45

Ala Pro Gly Gln Arg Phe Glu Trp Met Gly Gly Ile Ile Pro Ile Phe
    50                  55                  60

Asp Thr Ala Asn Tyr Ala Gln Lys Phe Gln Gly Arg Val Thr Ile Thr
65                  70                  75                  80

Ala Asp Glu Ser Thr Asn Thr Ala Tyr Met Glu Leu Ser Ser Leu Arg
                85                  90                  95

Ser Glu Asp Thr Ala Val Tyr Tyr Cys Ala Arg Gly Pro Glu Tyr Tyr
                100                 105                 110

Ala Tyr Val Trp Gly Ser Tyr Ser Tyr Asn Tyr Phe Asp Tyr Trp Gly

-continued

```
                115                 120                 125

Gln Gly Thr Leu Val Thr Val
    130                 135

<210> SEQ ID NO 29
<211> LENGTH: 135
<212> TYPE: PRT
<213> ORGANISM: Artificial Sequence
<220> FEATURE:
<223> OTHER INFORMATION: Synthetic

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Asn Asn Tyr
            20                  25                  30

Ala Thr Gly Asp Thr Phe Ser Asn Tyr Ala Ile Ser Trp Val Arg Gln
        35                  40                  45

Ala Pro Gly Gln Gly Phe Glu Trp Met Gly Gly Ile Ile Pro Ile Phe
    50                  55                  60

Asp Thr Ala Asn Tyr Ala Gln Lys Phe Gln Gly Arg Val Thr Ile Thr
65                  70                  75                  80

Ala Asp Glu Ser Thr Asn Thr Ala Tyr Met Glu Leu Ser Ser Leu Arg
                85                  90                  95

Ser Glu Asp Thr Ala Val Tyr Tyr Cys Ala Arg Gly Pro Glu Tyr Tyr
            100                 105                 110

Ala Tyr Val Trp Gly Ser Tyr Ser Tyr Asn Tyr Phe Asp Tyr Trp Gly
        115                 120                 125

Gln Gly Thr Leu Val Thr Val
    130                 135

<210> SEQ ID NO 30
<211> LENGTH: 114
<212> TYPE: PRT
<213> ORGANISM: Artificial Sequence
<220> FEATURE:
<223> OTHER INFORMATION: Synthetic

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Asp Asn Tyr Pro Ile Thr Phe Gly Gln Gly Thr Arg Leu Glu Ile
            100                 105                 110

Lys Arg

<210> SEQ ID NO 31
<211> LENGTH: 114
<212> TYPE: PRT
```

<213> ORGANISM: Artificial Sequence
<220> FEATURE:
<223> OTHER INFORMATION: Synthetic

<400> SEQUENCE: 31

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Asp Asn Tyr Pro Ile Thr Phe Gly Gln Gly Thr Arg Leu Glu Ile
            100                 105                 110
Lys Arg
```

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

```
Phe Ser Asn Tyr Ala Ile Ser
1               5
```

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

```
Phe Ser Asn Tyr Ala Ile Asn
1               5
```

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

```
Gly Asp Thr Phe Ser Asn Tyr Ile
1               5
```

<210> SEQ ID NO 35
<211> LENGTH: 29
<212> TYPE: DNA
<213> ORGANISM: Artificial Sequence
<220> FEATURE:
<223> OTHER INFORMATION: Synthetic

<400> SEQUENCE: 35
ctggaggcac cttcagcaac tatgctatc                                29

<210> SEQ ID NO 36
<211> LENGTH: 50
<212> TYPE: DNA
<213> ORGANISM: Artificial Sequence
<220> FEATURE:
<223> OTHER INFORMATION: Synthetic

<400> SEQUENCE: 36
ctggaggcac cttcagcaac tatgctatca ccttcagcaa ctatgctatc            50

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Thr Phe Ser Asn Tyr Ala Ile
1               5

<210> SEQ ID NO 38
<211> LENGTH: 29
<212> TYPE: DNA
<213> ORGANISM: Artificial Sequence
<220> FEATURE:
<223> OTHER INFORMATION: Synthetic

<400> SEQUENCE: 38
ctggaggcac cttcagcaac tatgctatc                                   29

<210> SEQ ID NO 39
<211> LENGTH: 56
<212> TYPE: DNA
<213> ORGANISM: Artificial Sequence
<220> FEATURE:
<223> OTHER INFORMATION: Synthetic

<400> SEQUENCE: 39
ctggagacac cttcagcaac tatgctactg gagacacctt cagcaactat gctatc     56

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Gly Asp Thr Phe Ser Asn Tyr Ala
1               5

<210> SEQ ID NO 41
<211> LENGTH: 46
<212> TYPE: DNA
<213> ORGANISM: Artificial Sequence
<220> FEATURE:
<223> OTHER INFORMATION: Synthetic

<400> SEQUENCE: 41
caggtgcagc tggttcagtc tggggctgag gtgaagaagc ctgggt                46

<210> SEQ ID NO 42
<211> LENGTH: 74
<212> TYPE: DNA

```
<213> ORGANISM: Artificial Sequence
<220> FEATURE:
<223> OTHER INFORMATION: Synthetic

<400> SEQUENCE: 42
caggtgcagc tggttcagtc tggggctgag gtgaactggg tgcagctggt tcagtctggg      60
gctgaggtga agaa                                                       74

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Asn Trp Val Gln Leu Val Ala Ser Gly Gln Glu Val
1               5                   10
```